United States Patent [19]
Conway et al.

[11] Patent Number: 5,599,321
[45] Date of Patent: *Feb. 4, 1997

[54] SUSTAINED RELEASE BACTERICIDAL CANNULA

[75] Inventors: Anthony J. Conway; Philip J. Conway, both of Chatfield; Richard D. Fryar, Jr., Rochester, all of Minn.

[73] Assignee: Rochester Medical Corporation, Stewartville, Minn.

[*] Notice: The term of this patent shall not extend beyond the expiration date of Pat. No. 5,261,896.

[21] Appl. No.: 484,600

[22] Filed: Jun. 7, 1995

Related U.S. Application Data

[62] Division of Ser. No. 148,995, Nov. 8, 1993, Pat. No. 5,482,740, which is a division of Ser. No. 809,281, Dec. 13, 1991, Pat. No. 5,261,896, which is a continuation-in-part of Ser. No. 489,462, Mar. 6, 1990, abandoned, which is a continuation-in-part of Ser. No. 487,422, Mar. 1, 1990, Pat. No. 5,098,379, which is a continuation-in-part of Ser. No. 462,832, Jan. 10, 1990, Pat. No. 5,137,671.

[51] Int. Cl.⁶ ............... A61M 5/32; A61M 25/00
[52] U.S. Cl. ............... 604/265; 427/2.3; 424/430
[58] Field of Search ............... 427/2.3, 2.28, 427/387; 604/265, 264; 424/422, 426, 430

[56] References Cited

U.S. PATENT DOCUMENTS

| | | |
|---|---|---|
| 1,235,142 | 7/1917 | Ichilian . |
| 1,643,289 | 8/1927 | Peglay . |
| 2,043,630 | 6/1936 | Raiche . |
| 2,230,226 | 4/1941 | Auzin . |
| 2,248,934 | 7/1941 | Auzin . |
| 2,308,484 | 1/1943 | Auzin et al. . |

(List continued on next page.)

FOREIGN PATENT DOCUMENTS

| | | |
|---|---|---|
| 763930 | 7/1967 | Canada . |
| 0055023 | 6/1982 | European Pat. Off. . |
| 0184629 | 6/1986 | European Pat. Off. . |

(List continued on next page.)

OTHER PUBLICATIONS

"The Merck Index: Ninth Edition", 1976, Merck and Co., Inc., p. 857 (no month).
Bayston, "The Antibacterial Effects of Impregnated Silastic and its Possible Applications in Surgery", *J. Pediatric Surgery,* 12, 55–61 (1977). Feb.

(List continued on next page.)

*Primary Examiner*—Diana Dudash
*Attorney, Agent, or Firm*—Merchant, Gould, Smith, Edell, Welter & Schmidt

[57] ABSTRACT

A sustained release bactericidal cannula or catheter for residence within a portion of a human body through which aqueous biological fluids can pass. The bactericidal cannula for catheter including a tube having an inner surface, defining and interior lumen, and an outer surface. The tube has a polymeric matrix and antibacterial agent residing within at least a portion of the polymeric matrix. The polymeric matrix includes cured silicon rubber and the antibacterial agent is a finely divided nitrofuran compound which is soluble in water and effective to prevent proliferation of certain bacteria in an otherwise growth supporting aqueous environment when dissolved in the aqueous environment to the limit of its solubility therein at 37° C. The solubility of the nitrofuran compound is preferably about 0.2% by weight or less at a pH of about 6 and a temperature of about 25° C. The antibacterial agent can diffuse out of the polymeric matrix and into an aqueous biological environment when the polymeric matrix comes into contact with such an aqueous biological environment. Preferably, at least a finite portion of the polymeric matrix proximate the outer surface includes an amount of from about 10 to about 60% by weight of the nitrofuran compound and the amount of the nitrofuran compound and the solubility thereof cooperate to provide a potential for a sustained release diffusion thereof for a period of not less than about three weeks during normal use of the cannula within the human body. Methods of making a sustained release bactericidal cannula and of catheterizing a patient are also disclosed.

8 Claims, 18 Drawing Sheets

U.S. PATENT DOCUMENTS

| | | | |
|---|---|---|---|
| 2,314,262 | 3/1943 | Winder . | |
| 2,320,157 | 5/1943 | Raiche | 128/349 |
| 2,322,858 | 6/1943 | Limbert et al. . | |
| 2,330,399 | 9/1943 | Widner . | |
| 2,330,400 | 9/1943 | Winder . | |
| 2,390,070 | 12/1945 | Auzin . | |
| 2,481,488 | 9/1949 | Auzin . | |
| 2,690,595 | 10/1954 | Raiche . | |
| 2,712,161 | 7/1955 | Moss . | |
| 3,044,468 | 7/1962 | Birtwell . | |
| 3,053,257 | 9/1962 | Birtwell . | |
| 3,169,527 | 2/1965 | Sheridan . | |
| 3,304,353 | 2/1967 | Harautuneian . | |
| 3,394,705 | 7/1968 | Abramson . | |
| 3,409,016 | 11/1968 | Foley . | |
| 3,463,141 | 8/1969 | Mozolf . | |
| 3,503,400 | 3/1970 | Osthagen et al. . | |
| 3,508,959 | 4/1970 | Krahnke . | |
| 3,539,674 | 11/1970 | Dereniuk et al. . | |
| 3,544,668 | 12/1970 | Dereniuk . | |
| 3,556,294 | 1/1971 | Walck, III et al. . | |
| 3,566,874 | 3/1971 | Shepherd et al. . | |
| 3,593,713 | 7/1971 | Bogoff et al. . | |
| 3,598,127 | 8/1971 | Wepsic . | |
| 3,606,889 | 9/1971 | Arblaster . | |
| 3,642,004 | 2/1972 | Osthagen et al. . | |
| 3,683,928 | 8/1972 | Kuntz . | |
| 3,695,921 | 10/1972 | Shepherd et al. . | |
| 3,699,956 | 10/1972 | Kitrilakis et al. . | |
| 3,708,324 | 1/1973 | Stebleton . | |
| 3,797,478 | 3/1974 | Walsh et al. | 128/1 R |
| 3,841,304 | 10/1974 | Jones . | |
| 3,854,483 | 12/1974 | Powers . | |
| 3,875,937 | 4/1975 | Schmitt et al. . | |
| 3,879,516 | 4/1975 | Wolvek . | |
| 3,889,685 | 6/1975 | Miller, Jr. et al. . | |
| 3,894,540 | 7/1975 | Bonner, Jr. . | |
| 3,924,634 | 12/1975 | Taylor et al. . | |
| 3,926,705 | 12/1975 | Todd . | |
| 3,981,299 | 9/1976 | Murray . | |
| 4,029,104 | 6/1977 | Kerber | 128/348 |
| 4,062,363 | 12/1977 | Bonner et al. . | |
| 4,133,303 | 1/1979 | Patel . | |
| 4,149,539 | 4/1979 | Cianci . | |
| 4,196,731 | 4/1980 | Laurin et al. . | |
| 4,198,984 | 4/1980 | Taylor . | |
| 4,249,535 | 2/1981 | Hargest, III . | |
| 4,265,848 | 5/1981 | Rüsch . | |
| 4,266,999 | 5/1981 | Baler | 427/2.3 |
| 4,269,310 | 5/1981 | Uson . | |
| 4,284,459 | 8/1981 | Patel et al. . | |
| 4,318,947 | 3/1982 | Joung . | |
| 4,378,796 | 4/1983 | Milhaud . | |
| 4,381,008 | 4/1983 | Thomas et al. . | |
| 4,381,380 | 4/1983 | LeVeen et al. . | |
| 4,457,299 | 7/1984 | Cornwell . | |
| 4,472,226 | 8/1984 | Redinger et al. . | |
| 4,479,795 | 10/1984 | Mustacich et al. . | |
| 4,515,593 | 5/1985 | Norton . | |
| 4,539,234 | 9/1985 | Sakamoto et al. . | |
| 4,553,533 | 11/1985 | Leighton . | |
| 4,563,184 | 1/1986 | Korol . | |
| 4,571,239 | 2/1986 | Heyman . | |
| 4,571,240 | 2/1986 | Samson et al. . | |
| 4,581,028 | 4/1986 | Fox, Jr. et al. . | |
| 4,582,762 | 4/1986 | Onohara et al. . | |
| 4,592,920 | 6/1986 | Murtfeldt . | |
| 4,601,713 | 7/1986 | Fugua . | |
| 4,603,152 | 7/1986 | Laurin et al. . | |
| 4,612,337 | 9/1986 | Fox, Jr. et al. . | |
| 4,622,033 | 11/1986 | Taniguchi . | |
| 4,623,329 | 11/1986 | Drobish et al. . | |
| 4,627,844 | 12/1986 | Schmitt . | |
| 4,634,433 | 1/1987 | Osborne . | |
| 4,652,259 | 3/1987 | O'Neil . | |
| 4,664,657 | 5/1987 | Williamitis et al. . | |
| 4,677,143 | 6/1987 | Laurin et al. . | |
| 4,686,124 | 8/1987 | Onohara et al. . | |
| 4,687,470 | 8/1987 | Okada . | |
| 4,692,152 | 9/1987 | Emde . | |
| 4,710,169 | 12/1987 | Christopher . | |
| 4,710,181 | 12/1987 | Fuqua . | |
| 4,737,219 | 4/1988 | Taller et al. . | |
| 4,739,768 | 4/1988 | Engelson | 128/658 |
| 4,747,845 | 5/1988 | Korol . | |
| 4,769,013 | 9/1988 | Lorenz et al. . | |
| 4,772,473 | 9/1988 | Patel et al. . | |
| 4,775,371 | 10/1988 | Mueller, Jr. . | |
| 4,813,935 | 3/1989 | Haber et al. . | |
| 4,820,270 | 4/1989 | Hardcastle et al. | 264/167 |
| 4,820,292 | 4/1989 | Korol et al. . | |
| 4,838,876 | 6/1989 | Wong et al. . | |
| 4,850,969 | 7/1989 | Jackson . | |
| 4,861,337 | 8/1989 | George . | |
| 4,863,424 | 9/1989 | Blake, III et al. . | |
| 4,863,444 | 9/1989 | Blomer . | |
| 4,874,373 | 10/1989 | Luther | 604/164 |
| 4,902,503 | 2/1990 | Umemura et al. . | |
| 4,904,260 | 2/1990 | Ray et al. . | |
| 4,917,686 | 4/1990 | Bayston et al. . | |
| 4,923,450 | 5/1990 | Maeda et al. . | |
| 4,925,668 | 5/1990 | Kahn et al. . | |
| 4,930,522 | 6/1990 | Busnel et al. | 128/844 |
| 4,932,938 | 6/1990 | Goldberg . | |
| 4,935,260 | 6/1990 | Shienker . | |
| 4,950,256 | 8/1990 | Luther et al. . | |
| 4,968,507 | 11/1990 | Zentner et al. . | |
| 4,976,703 | 12/1990 | Franetzki et al. . | |
| 4,981,471 | 1/1991 | Quinn et al. . | |
| 4,994,047 | 2/1991 | Walker et al. . | |
| 5,013,306 | 5/1991 | Solomon et al. . | |
| 5,013,717 | 5/1991 | Solomon et al. . | |
| 5,019,096 | 5/1991 | Fox, Jr. et al. . | |
| 5,019,378 | 5/1991 | Allen . | |
| 5,019,601 | 5/1991 | Allen . | |
| 5,082,006 | 1/1992 | Jonasson | 128/885 |
| 5,089,205 | 2/1992 | Huang et al. | 427/2.3 |
| 5,090,424 | 2/1992 | Simon et al. | 128/885 |
| 5,098,379 | 3/1992 | Conway et al. | 604/51 |
| 5,112,306 | 5/1992 | Burton | 604/101 |
| 5,131,906 | 7/1992 | Chen | 600/29 |
| 5,137,671 | 8/1992 | Conway et al. | 264/130 |
| 5,165,952 | 11/1992 | Solomon et al. | 427/2 |
| 5,176,666 | 1/1993 | Conway et al. | 427/2.3 |
| 5,261,896 | 11/1993 | Conway et al. | 604/265 |
| 5,290,306 | 3/1994 | Trotta et al. | 606/194 |
| 5,306,226 | 4/1994 | Salama | 600/29 |
| 5,360,402 | 11/1994 | Conway et al. | 604/97 |
| 5,370,899 | 12/1994 | Conway et al. | 427/2.3 |
| 5,451,424 | 9/1995 | Solomon et al. | 427/2.3 |
| 5,464,650 | 11/1995 | Berg et al. | 427/2.28 |

FOREIGN PATENT DOCUMENTS

| | | | |
|---|---|---|---|
| 0303487 | 2/1989 | European Pat. Off. . | |
| 2351634 | 12/1977 | France . | |
| 352014 | 4/1922 | Germany | 128/842 |
| 41-35502 | 2/1993 | Germany . | |
| 278468 | 5/1970 | U.S.S.R. . | |
| 2150938 | 7/1985 | United Kingdom . | |
| 84/01102 | 3/1984 | WIPO . | |
| 89/09626 | 1/1989 | WIPO . | |
| 90/04431 | 5/1990 | WIPO . | |

| | | |
|---|---|---|
| WO91/10466 | 7/1991 | WIPO . |
| WO92/08426 | 5/1992 | WIPO . |
| WO93/14806 | 8/1993 | WIPO . |

OTHER PUBLICATIONS

Bayston, "Preliminary Studies on the Impregnation of Silastic Elastomers with Antimicrobial Substances,", *Devel. Medicine and Child Neurol.*, Supply. (37):50–54 (1976) (no month available).

Butler et al., "Evaluation of Polymyxin Catheter Lubricant and Impregnated Catheters", *J. Urology*, 100, 560–566 (1968). Oct.

S. M. Lazarus et al., "A Hydrophilic Polymer–Coated Antimicrobial Urethral Catheter", *J. Biomed. Mater. Res.*, 5, 129–138 (1971). (no month available).

J. C. Brocklehurst et al., "The Management of Indwelling Catheters", *Brit. J. Urology*, 50(2): 102–105 (1978) (no month available).

A. M. Johansen and B. Sorensen, "Scand. J. Plast. Reconstr. Surg." 6(1): 47–50 (1972) (no month available).

K. Miura et al., "The Nitrofurans, in Progress in Medicine Chemistry"; vol. 5(G.P. Ellis & G.B. West, Eds.); 1967; New York, N.Y.; Plenum; pp. 320–381 (no month available).

T. Monson et al., "Evaluation of a Polymer–coated Indwelling Catheter in Prevention of Infection", *J. Urology*, 111:220–222 (1974). Feb.

I. Sakamoto et al., *"Efficacy of an Antibiotic Coated Indwelling Catheter: A Preliminary Report"*, *J. Biomed Materials Res.* 19: 1031–1041 (1985) (no month available).

Z. Shah et al., "Capsular Contracture Around Silicone Implants: The role of Intraluminal Antibiotics", *Plastic and Reconstr. Surg.*, 69: 809–814 (1982). May.

R. Van Noort, "Mechanical Properties of Antibacterial Silicone Rubber for Hydrocephalus Shunts", *J. Biomed. Materials Res.*, 13: 623–630 (1979) (no month available).

H. Mooro et al., "Prevention of Catheter Fever by the Use of Fruacin Uretheral Inserts", *J. Egypt Med. Assoc. (Egypt)* 49(8): 550–553 (1966) (no month available).

J. L. Nosher et al., "Antibiotic bonded Nephrostomy Catheters for Percutaneious Nephrostomies", *Cardiovasc. Interventional Radiol.* 13: 102–106 (1990) (no month available).

M. Rehula, *Cesk. Farm.* (Czechoslovakia ) 39/10: 436–437 (1990). abstract only, (no month).

M. Rehula, *Cesk. Farm.* (Czechoslovakia) 39/8: 349–352 (1990). English abstract only, (no month).

D. N. Rushton et al., "Implant Infections and Antibiotic–Impregnated Silicone Rubber Coating", *J. Neurol Neurosurg., Psych.*, 52: 223–229 (1989) (no month available).

The Bard Hospital Division brochure (copyright on a date unknown prior to Nov. 19, 1989 by C. R. Bard, Inc., Murray Hill, N.J. 07974.

*Kurt K. Nielsen et al., "The Urethral Plug: A New Treatment Modality for Genuine Urinary Stress Incontinence in Women", *The Journal of Urology*, vol. 144, No. 5, Nov. 1990, pp. 1199–1202.

*K. K. Nielsen et al., "The Uretheral Plug II: An Alternative Treatment in Women with Genuine Urinary Stress Incontinence", *British Journal of Urology*, (1993) 72, 428–432 (no month available).

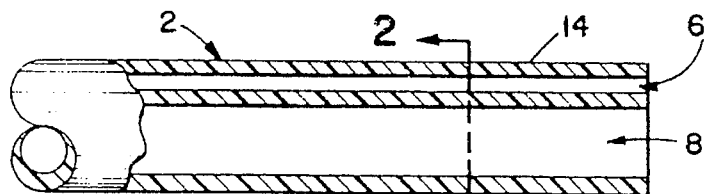 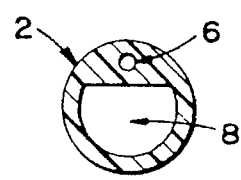
FIG. 1  FIG. 2
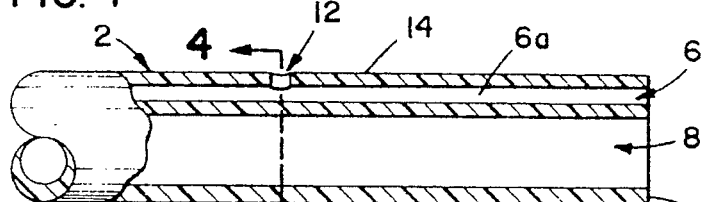 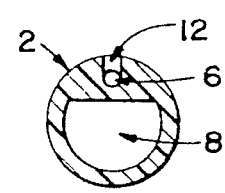
FIG. 3  FIG. 4
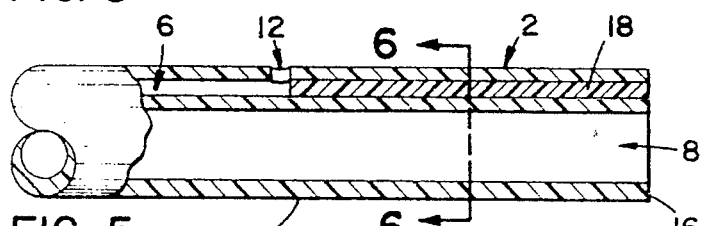 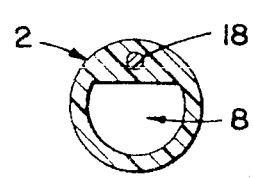
FIG. 5  FIG. 6
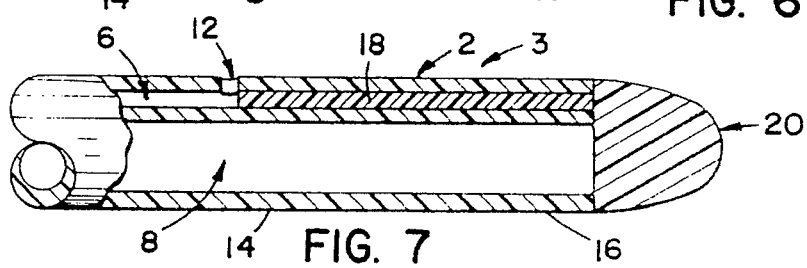
FIG. 7
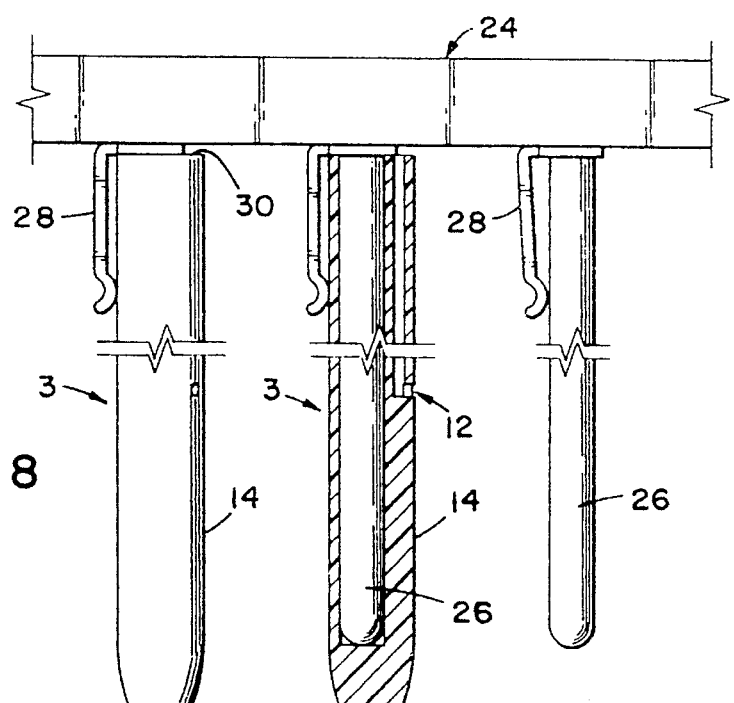
FIG. 8

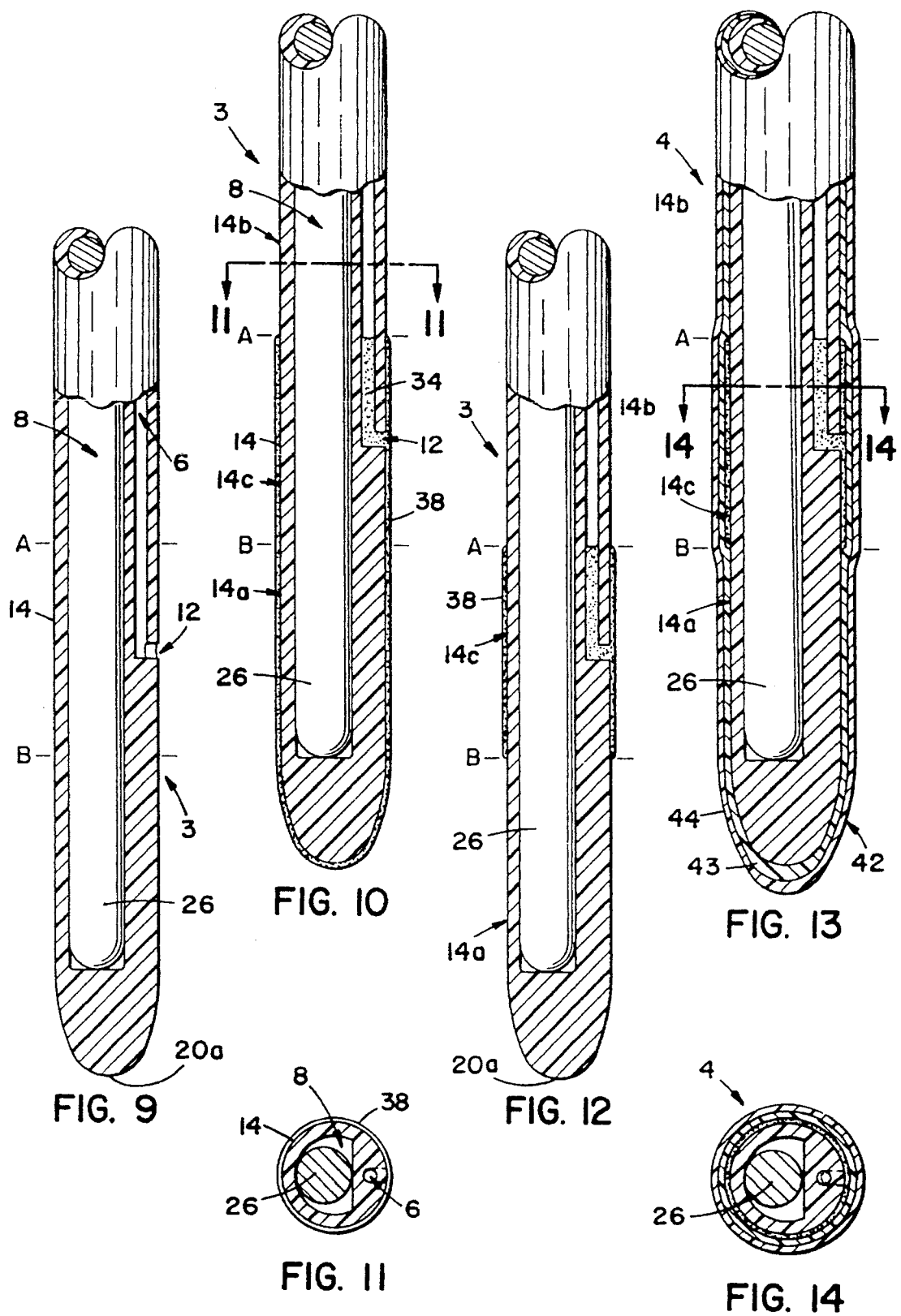

FIG. 15
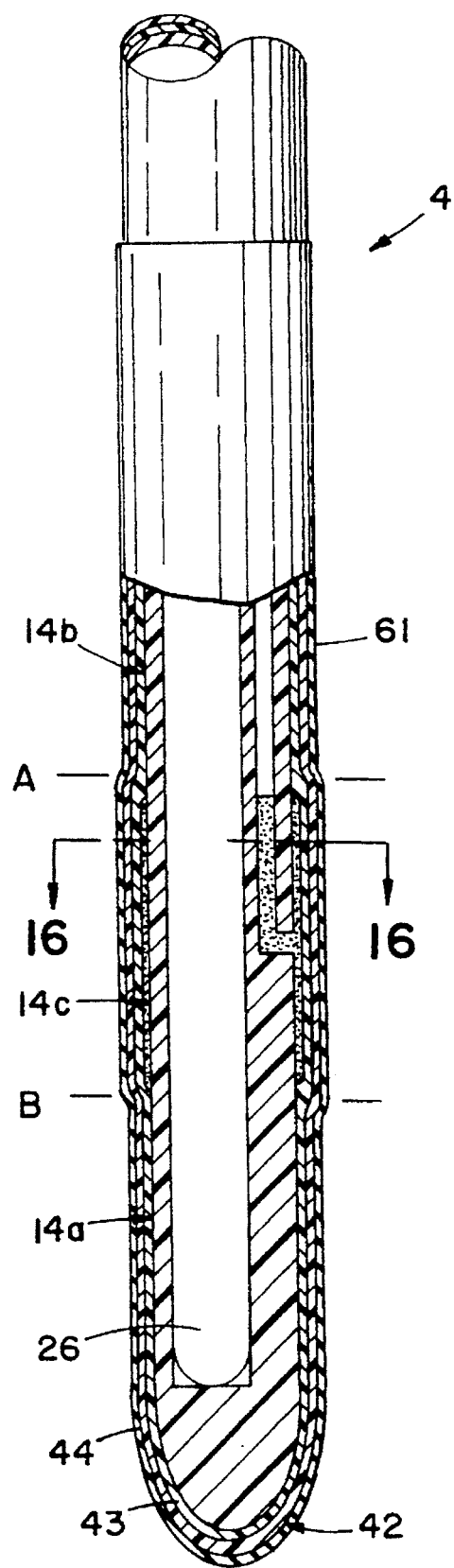
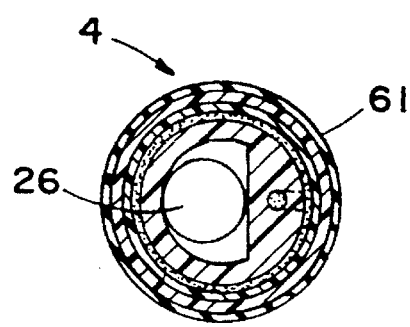
FIG. 16

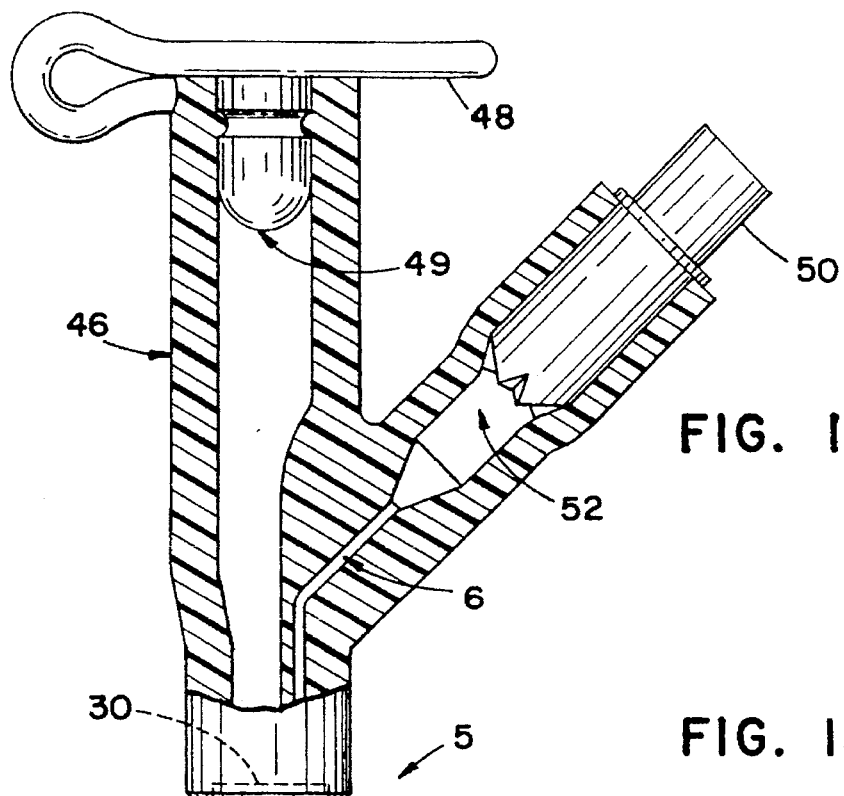
FIG. 17
FIG. 18
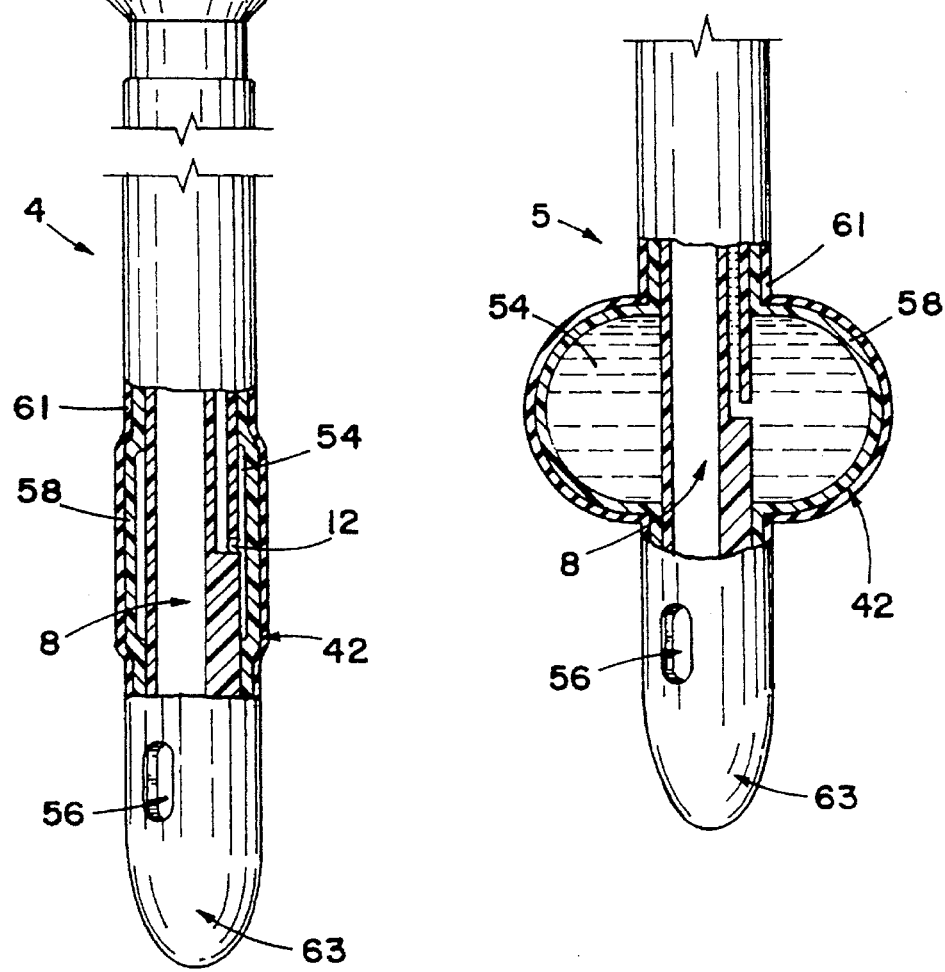

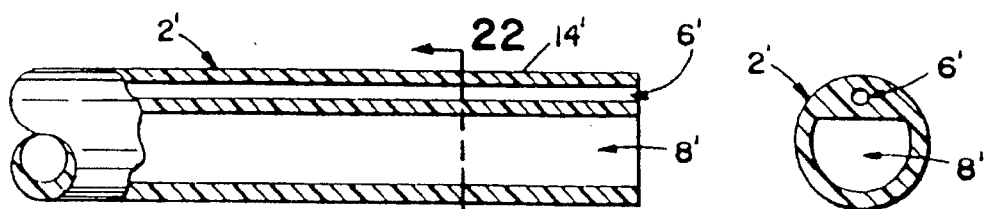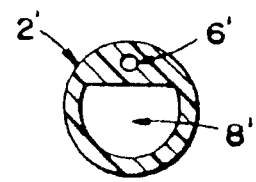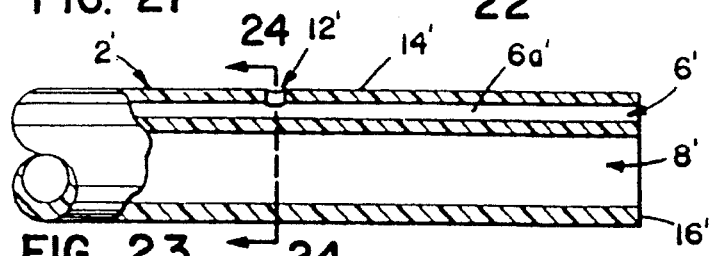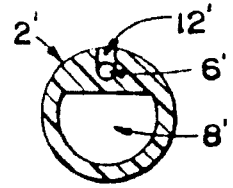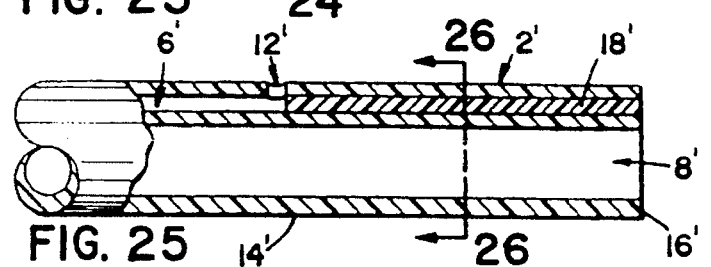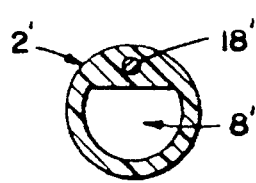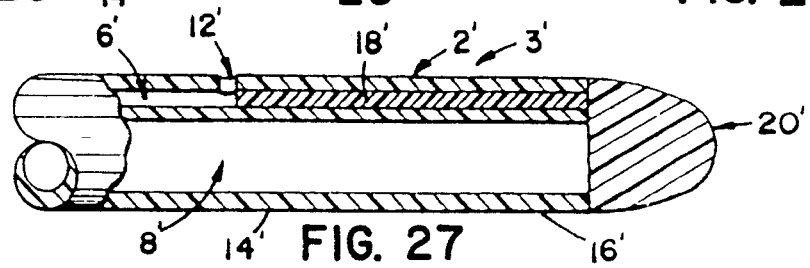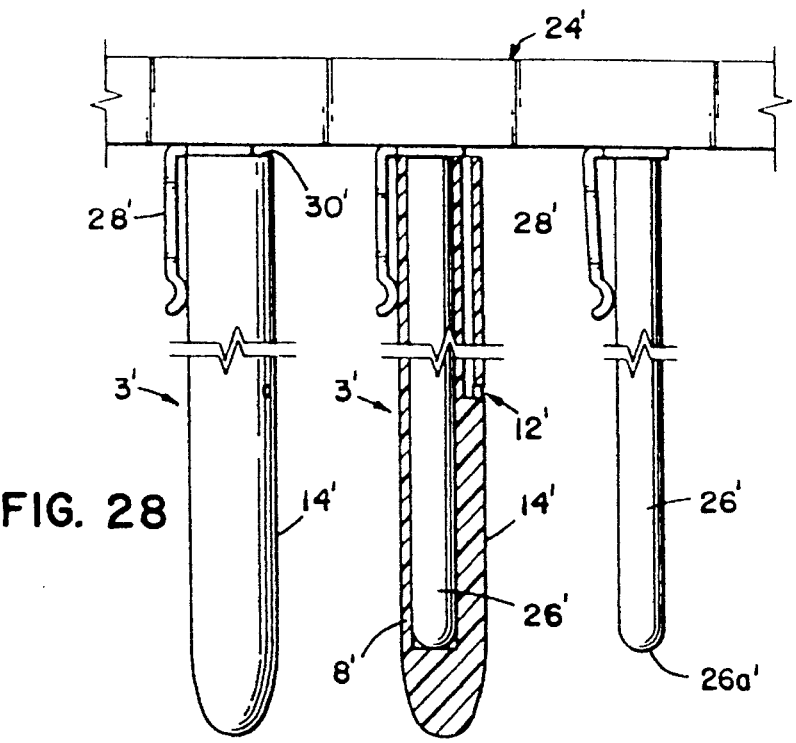

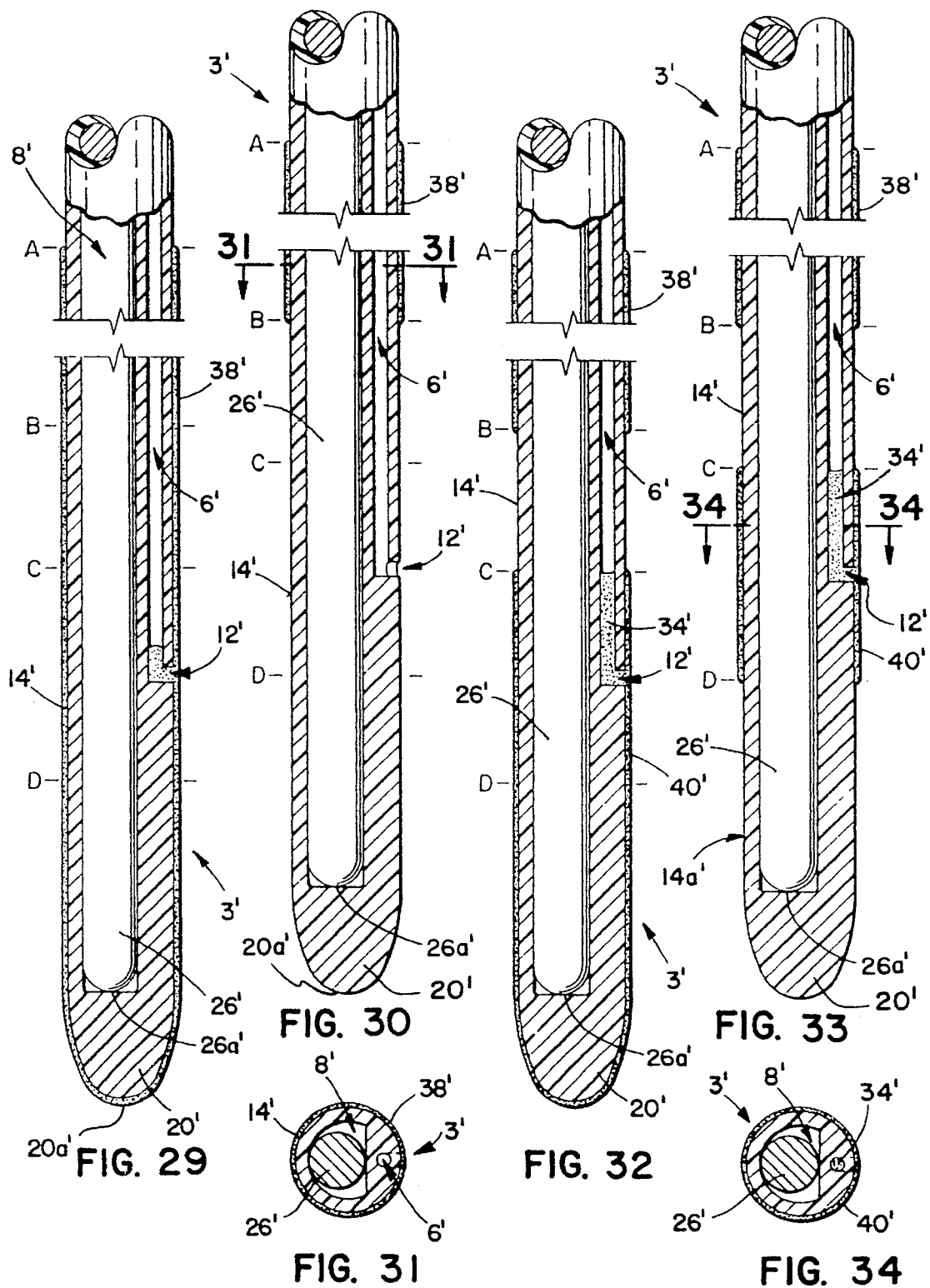

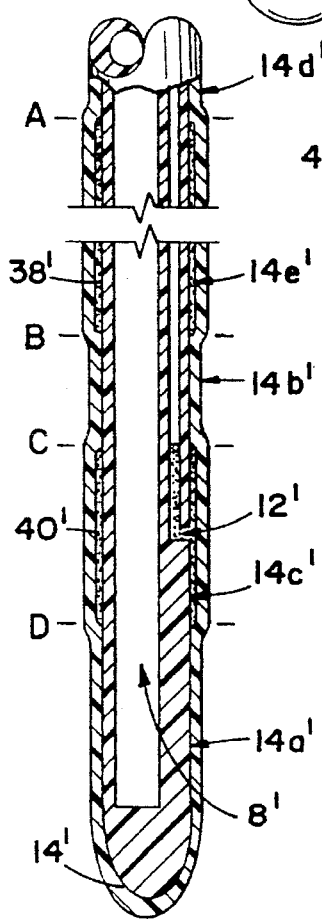
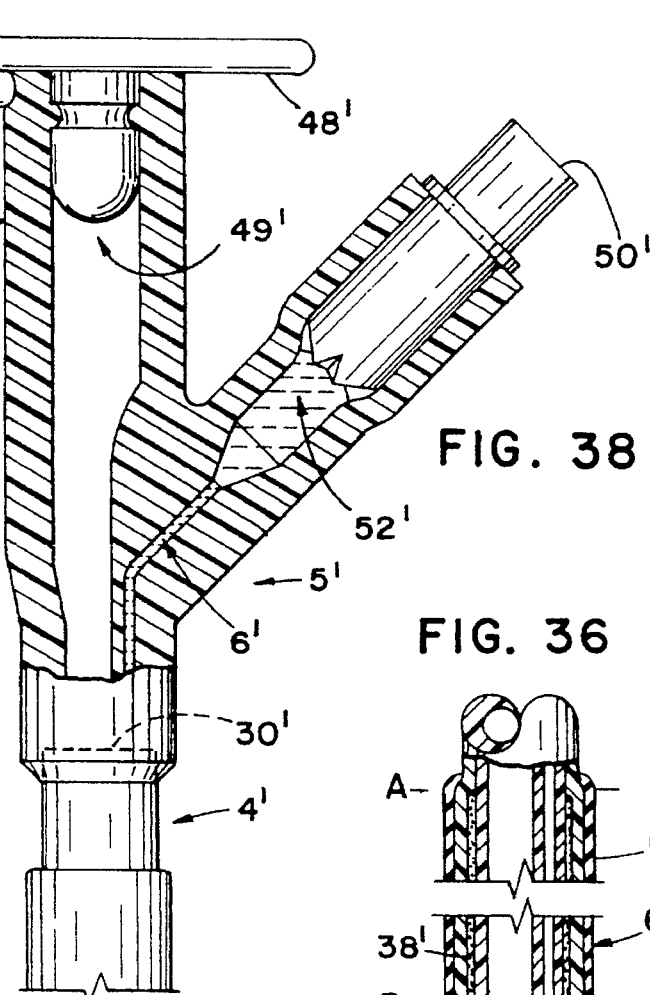
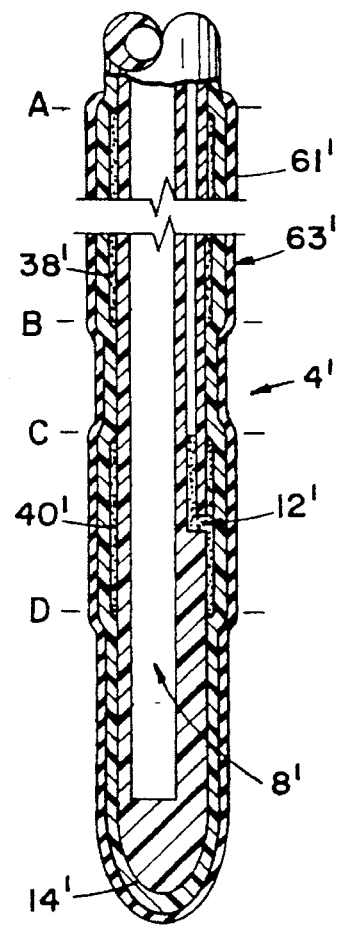
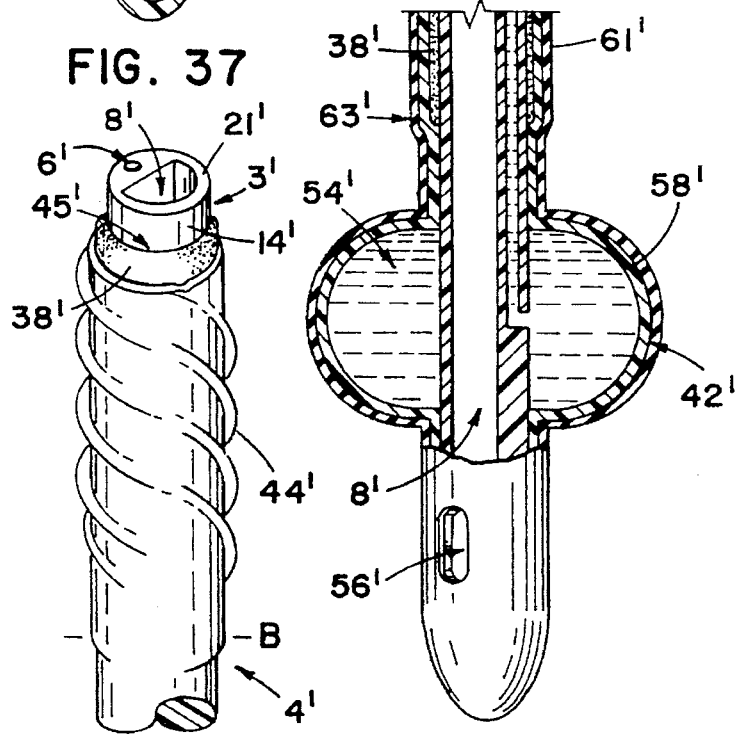

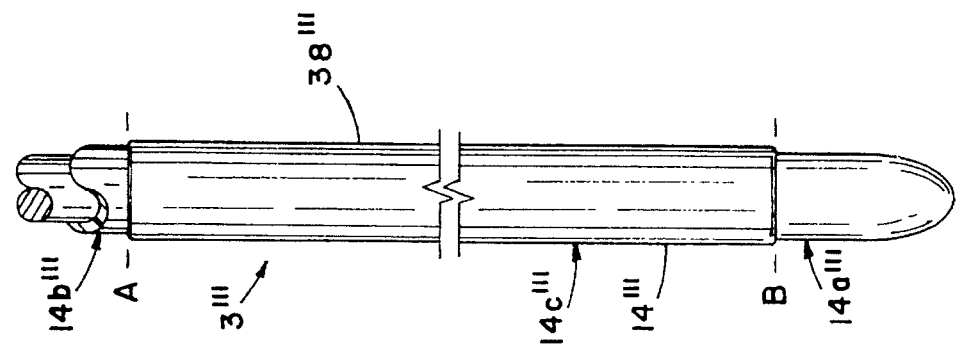
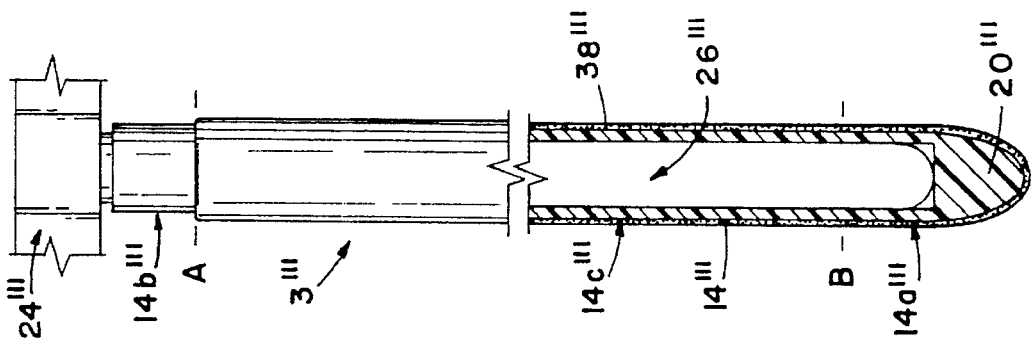
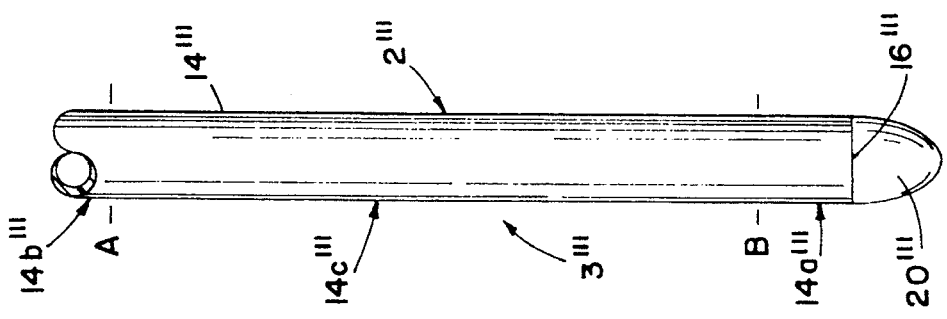
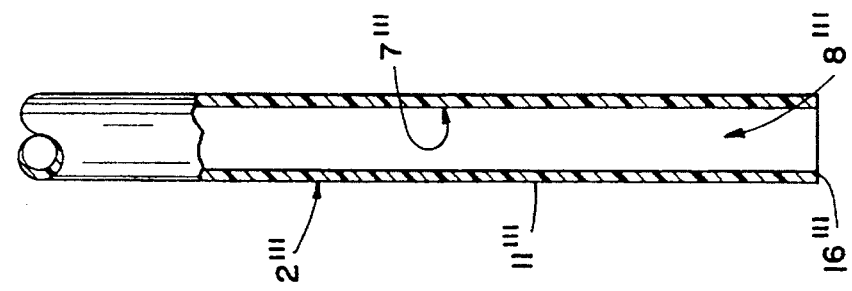

SUSTAINED RELEASE BACTERICIDAL CANNULA

CROSS-REFERENCE TO OTHER APPLICATIONS

The present application is a divisional application of U.S. patent application Ser. No. 08/148,995, filed Nov. 8, 1993, now U.S. Pat. No. 5,482,740 which a divisional application of U.S. patent application Ser. No. 07/809,281, filed Dec. 13, 1991, now U.S. Pat. No. 5,261,896 which is a continuation-in-part application of U.S. patent application Ser. No. 07/489,462, filed Mar. 6, 1990, now abandoned, which is a continuation-in-part application of U.S. patent application Ser. No. 07/487,422, filed Mar. 1, 1990, now U.S. Pat. No. 5,098,379 which is a continuation-in-part application of U.S. patent application Ser. No. 07/462,832, filed Jan. 10, 1990, now U.S. Pat. No. 5,137,671 the disclosures of which are each incorporated herein by reference.

FIELD OF THE INVENTION

The present invention relates to sustained release bactericidal cannulas or catheters which are either implantable or insertable into a human body. These devices have an antibacterial agent incorporated within the device which diffuse out in situ to prevent the proliferation or colonization of bacteria in regions adjacent to the exterior of the cannula or catheter. The present invention also relates to methods for making the same, products made by these methods, and methods of using the sustained release bactericidal cannulas or catheters, to prevent proliferation, colonization or continued viability of a bacterial population in regions adjacent TO the exterior of the respective cannula or catheter.

BACKGROUND OF THE INVENTION

Most catheters are a cannula or tube like device which is inserted into a portion of a person's body in order to transport fluids or gases in or out of that particular portion of the body. In passing through any particular portion of the body in order to reach its destination, the catheter will come into contact with various tissues in the body. For example, a catheter used to drain one'bladder (such as a "Foley" catheter) must pass through the urethral tract in order to reach the bladder. A nasogastric catheter must pass through the nasal passageway and the esophagus in order to reach the stomach. Some catheters, such as these, are inserted through existing passageways in order to reach their destinations, while others are inserted through surgically created passageways.

In virtually every catheterization, there is a significant potential for microbial growth along the exterior surface of the catheter which can lead to serious infections such as urinary tract infections, bladder infections and the like. Such an infection can be encouraged when adjacent tissues are inflamed due to irritation from rubbing a chafing against this catheter. This is because inflamed or irritated tissues may be less apt to respond effectively to suppress local bacterial infection. In such a situation the infection can spread and intensify, placing the patient at further risk. Such infections can lead to sepsis of the bladder particularly in elderly patients who are incontinent and have a chronic need for catheterization with an indwelling self-retaining catheter such as a "Foley" catheter. Long-term use of indwelling urinary catheters in nursing home patients is well known as a potential cause of significant morbidity due to such infections.

This problem is widely recognized and many solutions for this problem have been suggested in the past. None of these solutions, however, have been completely free of secondary complications and/or completely successful in eliminating the problem. For instance, systemic use of antibacterial drugs or agents have been tried. However, these drugs generally have undesirable secondary effects upon the patient when used systemically, especially when there is a chronic need for catheterization and the drug must employed for a long period of time. Local use of such drugs or agents can be effective for a short period of time, but has not been found to be effective for long-term use for a number of reasons. First, the drug or agent is easily washed out if there is a leakage of urine through the urinary track outside of the catheter. Second, the drug or agent may be delivered only to certain areas of the urinary tract and, third, the drug or agent may be absorbed by the body tissues adjacent to the catheter and transported elsewhere within the body.

Other methods of preventing periurethral contamination have been suggested. These include careful cleansing of the periurethral area on a routine basis, impregnating a sponge or the like with an antiseptic solution and retaining it in a position proximate the urethral, apply antimicrobial ointments to an external portion of the urinary tract, intraurethral irrigation of the urinary track through a separate channel, lubrication of the catheter with an antibiotic-containing material and the use of catheters impregnated with antimicrobial agents. Each of these methods has been explored and none have been found to be entirely satisfactory. In vitro tests of impregnated catheters indicate that the antibacterial agents within the catheters have a tendency to leach or diffuse out of the catheters in a short period of time. Often, the antibacterial activity was either gone or markedly diminished within 24 to 48 hours of insertion within the urethral tract. Therefore, it would be appreciated that a sustained release bactericidal cannula or catheter is needed in order to address the needs of patients requiring long-term catheterization or the like.

Accordingly, it will be appreciated that there is a need for a medical device, cannula or catheter which will address these and other problems associated with the prior art devices. The present invention provides advantages over the prior art cannulas and catheters, over the prior art methods for manufacturing the same, and also offers other advantages over the prior art and solves other problems associated therewith.

SUMMARY OF THE INVENTION

Accordingly, a sustained release bactericidal cannula for residence within a portion of a human body through which aqueous biological fluids can pass is provided. The sustained release bactericidal cannula comprises a tube having an inner surface, defining an internal lumen, and an outer surface. The tube has a polymeric matrix and an antibacterial agent residing within at least a portion of the polymeric matrix, wherein the polymeric matrix preferably includes cured silicon rubber, said bacterial agent is preferably a finely divided nitrofuran which is soluble in water and effective to prevent proliferation of certain bacteria in an otherwise growth supporting aqueous environment when dissolved in the aqueous environment to the limit of its solubility therein at 37° C. Preferably the nitrofuran compound has a solubility of about 0.2% by weight or less in water at a pH of about 6 and a temperature of about 25° C. The antibacterial agent can diffuse out of the polymeric matrix and into an aqueous biological environment when the polymeric matrix comes into contact with such an aqueous biological environment. Preferably, at least a finite portion of the polymeric matrix proximate the outer surface preferably includes an amount of from about 10 to about 60% by weight of the nitrofuran compound, and the nitrofuran compound in the finite portion of the polymeric matrix and the solubility of the nitrofuran compound cooperate to provide a potential for a sustained release diffusion of the antibacterial agent into the aqueous biological fluids within the human body, during normal therapeutic use of the cannula therein, so long as the aqueous biological fluids are not saturated with the antibacterial agent, such that the antibacterial agent within the finite portion of the polymeric matrix can continue to diffuse into the aqueous biological fluids within the human body in an amount effective to prevent proliferation of certain bacteria immediately adjacent to the cannula in aqueous biological environments for a period of not less than about three weeks. In preferred embodiments the cannula is a urinary catheter for residence within a urinary track, preferably a "Foley" catheter having an expandable balloon cavity, a second lumen in communication with the expandable balloon cavity and a coating on at least a portion of the exterior surface of the catheter proximate the balloon cavity which is preferably a cured silicon rubber polymeric matrix incorporating an antibacterial agent capable of diffusing out of the polymeric matrix in aqueous environments. Preferably, the rate of diffusion of the antibacterial agent from the polymeric matrix can increase when the expandable balloon portion expands.

It is an object of the present invention to provide a sustained release bactericidal cannula or catheter which can be used on a long-term basis to reduce or eliminate the incidence of urinary tract infections in patients having a chronic need for catheterization. The present invention provides a catheter having a large percentage of active antibacterial agent incorporated into a cured silicon rubber outer coating. Preferably, the antibacterial agent is a finely divided nitrofuran compound having a solubility of about 0.2% by weight or less. In preferred embodiments the mean particle size of the nitrofuran compound particles is about 200 microns or less in order to allow for a very smooth outer surface on the cannula or catheter. This is important to reduce the incidence of irritation of the tissues within the urinary tract. It will be appreciated that it is especially difficult to incorporate a large percentage of a solid antibacterial agent within a polymeric matrix and still provide a smooth outer surface, as well as sufficient flexibility and durability so as to suitable for the intended use. In preferred embodiments of the present invention the mean particle size of the nitrofuran compound particles is about 100 microns or less enabling the incorporation of this antibacterial agent at an even higher percentage in the polymeric matrix, while still retaining the desired smoothness, flexibility and durability of the outer coating.

These and various other advantages and features of novelty which characterize the present invention are pointed out with particularity in the claims annexed hereto and forming a part hereof. However, for a better understanding of the present invention, its advantages and other objects obtained by its use, reference should be made to the drawings, which form a further part hereof, and to the accompanying descriptive matter, in which there is illustrated and described preferred embodiments of the present invention.

BRIEF DESCRIPTION OF THE DRAWINGS

In the drawings, in which like and primed, reference numerals indicate corresponding parts throughout the several views, FIG. 1 is a transverse schematic view of an extruded double lumen tube in partial cross-section;

FIG. 2 is a cross-sectional view of the extruded double lumen tube as seen from the line 2—2 of FIG. 1;

FIG. 3 is a transverse schematic view of the tube shown in partial cross-section in FIG. 1 after an opening is punched in the outer surface;

FIG. 4 is a cross-sectional view of the tube as shown from the line 4—4 of FIG. 3;

FIG. 5 is a transverse schematic view of the double lumen tube shown in partial cross-section in FIG. 3 after a portion of the first lumen has been filled with a polymeric bonding composition;

FIG. 6 is a cross-sectional view of the tube as seen from the line 6—6 of FIG. 5;

FIG. 7 is a transverse schematic view of the double lumen tube shown in partial cross-section in FIG. 5 after a tip is affixed to a distal end of the tube;

FIG. 8 is a schematic view of a portion of a rack used to retain a plurality of tubes during a series of dipping steps;

FIG. 9 is a transverse schematic view of an intermediate tube in partial cross-section similar to the tube shown in FIG. 7 at an intermediate stage of manufacture prior to the first of a series of dipping steps;

FIG. 10 is a transverse schematic view of an intermediate tube in partial cross-section similar to that shown in FIG. 9, but following a first dipping step wherein the outer surface is coated with a bond preventing agent up to the point designated by line A;

FIG. 11 is a cross-sectional view of the intermediate tube of FIG. 10 as shown from the line 11—11;

FIG. 12 is a view of an intermediate tube in partial cross-section similar to that shown in FIG. 10, but after a subsequent dipping step or steps in which the coating of bond preventing agent on a portion of the outer surface of the intermediate tube has been removed;

FIG. 13 is a transverse schematic view of a portion of a balloon catheter formed from the intermediate tube shown in FIG. 12 in partial cross-section, following a plurality of dipping steps to create an overcoat layer;

FIG. 14 is a cross-sectional view of the balloon catheter shown in FIG. 13 from the line 14—14;

FIG. 15 is transverse schematic view of a portion of a coated balloon catheter formed from the balloon catheter shown in FIG. 13 in partial cross-section, following a further coating step to create an outer bactericide release layer;

FIG. 16 is a cross-sectional view of the balloon catheter shown in FIG. 15 from the line 16—16;

FIG. 17 is a transverse schematic view of a Foley catheter made in accordance with the present invention following testing and cleaning and showing sectional views of portions thereof;

FIG. 18 is a schematic view of a portion of the Foley catheter shown in FIG. 15, but with the balloon portion of the catheter shown when expanded;

FIG. 21 is a transverse schematic view of an alternate extruded double lumen tube in partial cross-section;

FIG. 22 is a cross-sectional view of the alternate extruded double lumen tube as seen from the line 22—22 of FIG. 21;

FIG. 23 is a transverse schematic view of the alternate tube shown in FIG. 21 after an opening is punched in the outer surface;

FIG. 24 is a cross-sectional view of the alternate tube as shown from the line 24—24 of FIG. 23;

FIG. 25 is a transverse schematic view of the alternate double lumen tube shown in FIG. 23 after a portion of the first lumen has been filled with a polymeric bonding composition;

FIG. 26 is a cross-sectional view of the alternate tube as seen from the line 26—26 of FIG. 25;

FIG. 27 is a transverse schematic view of the alternate double lumen tube shown in FIG. 25 after a tip is affixed to a distal end of the tube;

FIG. 28 is a schematic view of a portion of a rack or pallet used to retain a plurality of tubes during a series of dipping steps;

FIG. 29 is a transverse schematic view of an alternate intermediate tube in partial cross-section similar to the alternate tube shown in FIG. 27 at an intermediate stage of manufacture following the first of a series of dipping steps which creates a coating of bond preventing lubricating agent on the outer surface;

FIG. 30 is a transverse schematic view of the alternate intermediate tube shown in FIG. 29, but following a second dipping step wherein the coating of bond preventing lubricating agent on the outer surface has been partially removed;

FIG. 31 is a cross-sectional view of the intermediate tube of FIG. 30 as shown from the line 31—31;

FIG. 32 is a transverse schematic view of the alternate intermediate tube shown in FIG. 30, but after a subsequent dipping step creating a second coating of bond preventing lubricating agent on a portion of the outer surface removed form the portion which remains coated by the first coating;

FIG. 33 is a transverse schematic view of the alternate intermediate tube shown in FIG. 32, but after yet another dipping step or step designed to remove the second coating from a further portion of the outer surface;

FIG. 34 is a cross-sectional view of the balloon catheter shown in FIG. 33 from the line 34—34;

FIG. 35 is a transverse schematic view of the intermediate tube shown in FIG. 33, following a further dipping step or steps to create an overcoat layer;

FIG. 36 is a transverse schematic view in partial cross-section of a portion of an alternate balloon catheter formed from the alternate intermediate tube shown in FIG. 35, following a further dipping step or steps to create an outer bactericide release layer;

FIG. 37 is a perspective view of a portion of the balloon catheter shown in FIG. 35 in partial cross-section, but wherein the balloon catheter has been severed through the sleeve cavity and the remaining portion of the sleeve has been twisted to demonstrate its independence of the outer surface of the extruded double lumen tube used to make the balloon catheter;

FIG. 38 is a transverse schematic view of the balloon catheter shown in FIG. 35, but in partial cross-section, but including an end piece and showing a sectional view of a portion of the catheter wherein the balloon portion of the catheter is expanded;

FIG. 43 is a transverse schematic view of another alternate extruded tube in partial cross-section;

FIG. 44 is a transverse schematic view of an alternate intermediate tube formed from the alternate extruded tube shown in FIG. 43;

FIG. 45 is a schematic view in partial cross-section of a portion of an alternate rack or pallet used to retain a plurality of alternate intermediate tubes during a series of steps designed to provide the tubes with overcoat layers of a polymeric bonding composition, wherein a single alternate intermediate tube like that shown in FIG. 44 is shown secured to a single support rod following a first dipping step wherein a portion of the outer surface of the alternate intermediate tube is coated with a bond preventing lubricating material;

FIG. 46 is a transverse schematic view of the alternate intermediate tube shown in FIGS. 43 and 44, but following a second dipping step wherein the coating of bond preventing lubricating material on the outer surface of the alternate intermediate tube has been partially removed;

DETAILED DESCRIPTION OF THE PREFERRED EMBODIMENTS

Figure 39:
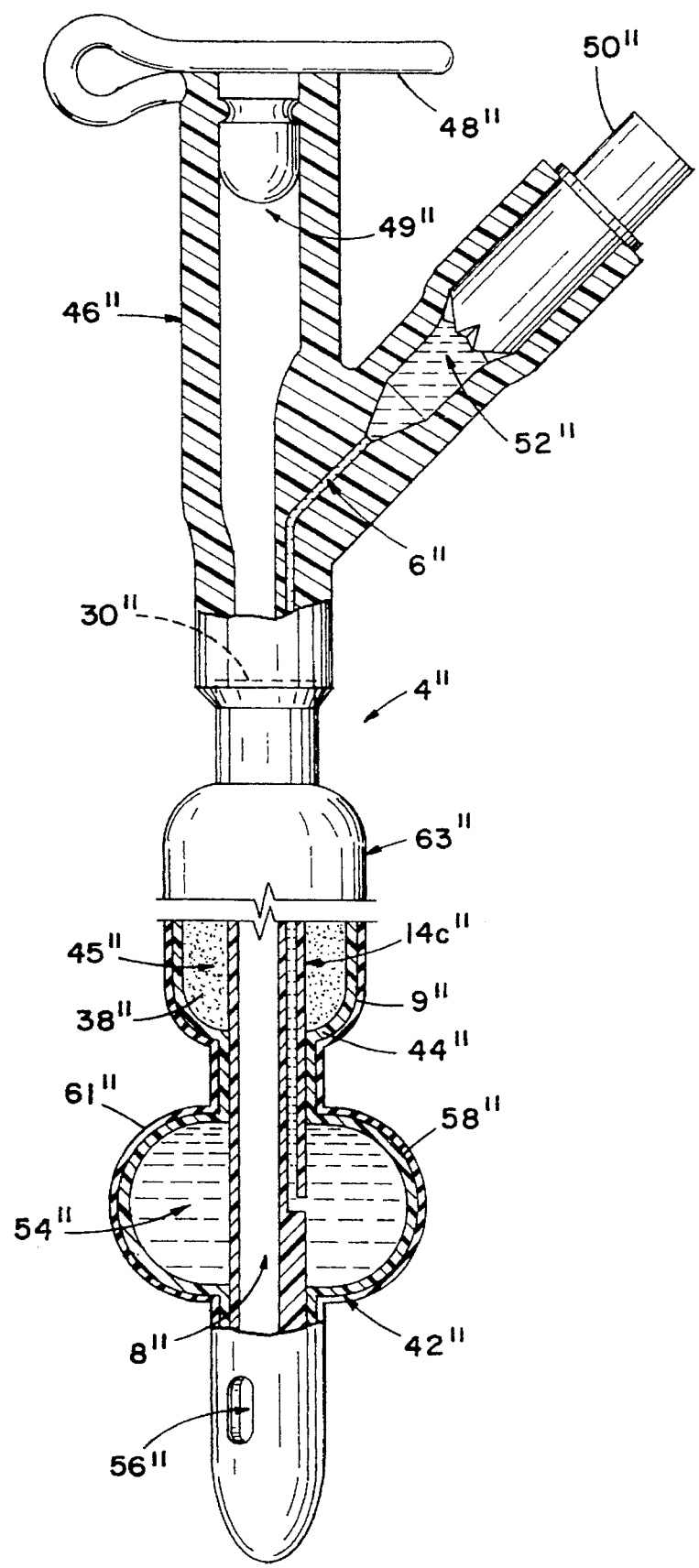
FIG. 39 is a transverse schematic view in partial cross-section of yet another embodiment of the present invention similar to that shown in FIG. 38.
Figure 40:
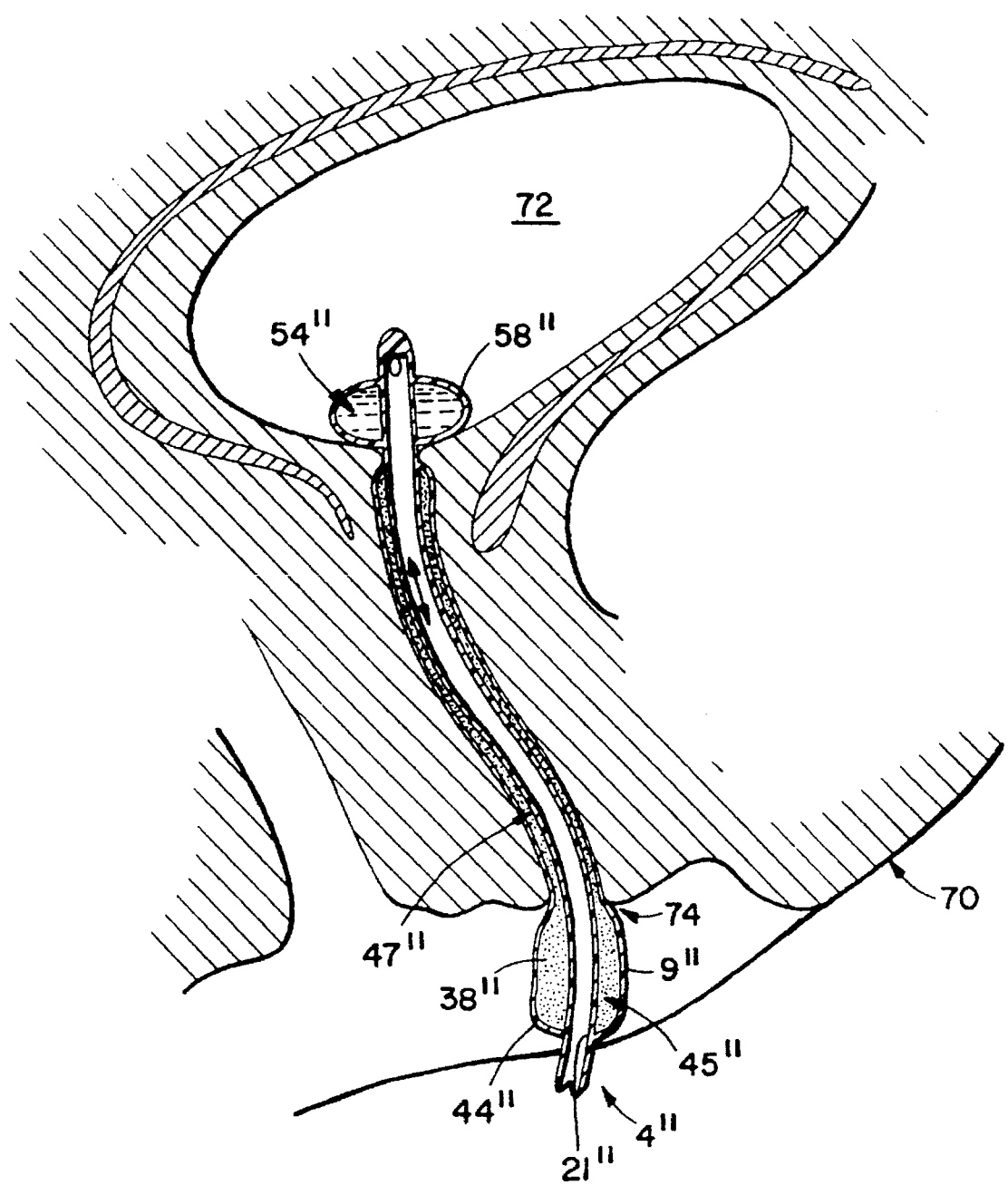
FIG. 40 is a transverse schematic sectional view showing a portion of the catheter shown in FIG. 39 when inserted in a urethral tract.
Figure 41:
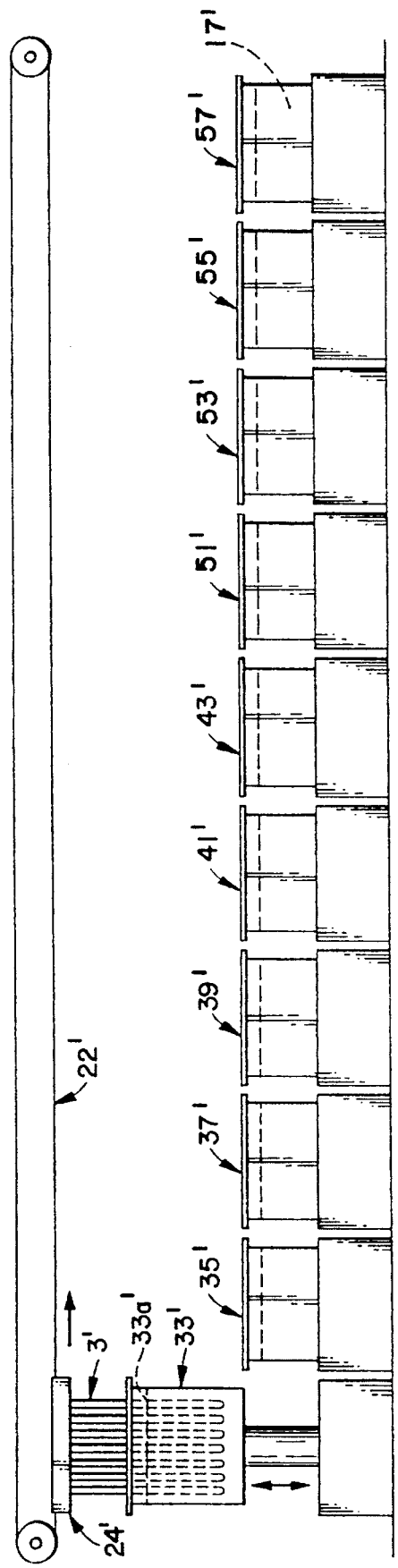
FIG. 41 is a schematic illustration of apparatus used to automate the production of catheters in accordance with the present invention.
Figure 48:
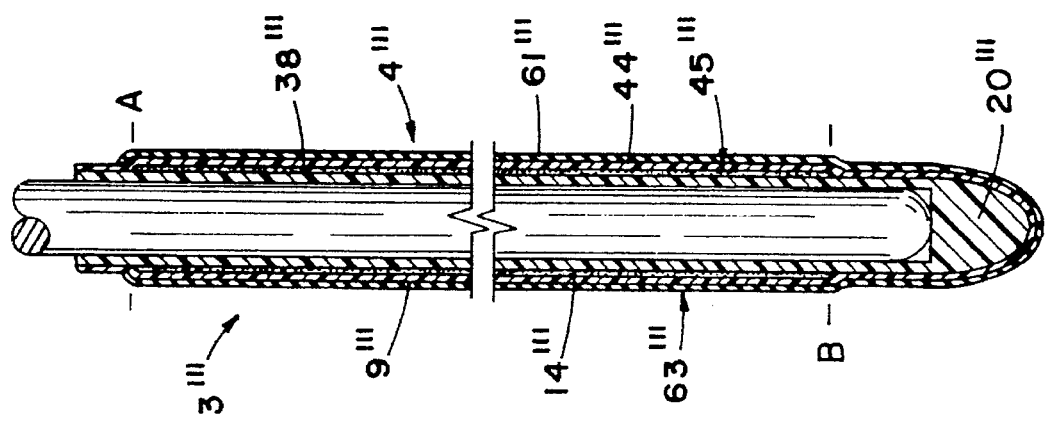
FIG. 48 is a transverse sectional schematic view of the alternate intermediate tube shown in FIG. 47 following a subsequent dipping step or steps in which an outer bactericide release layer is formed over a portion of the overcoat layer.
Figure 49:
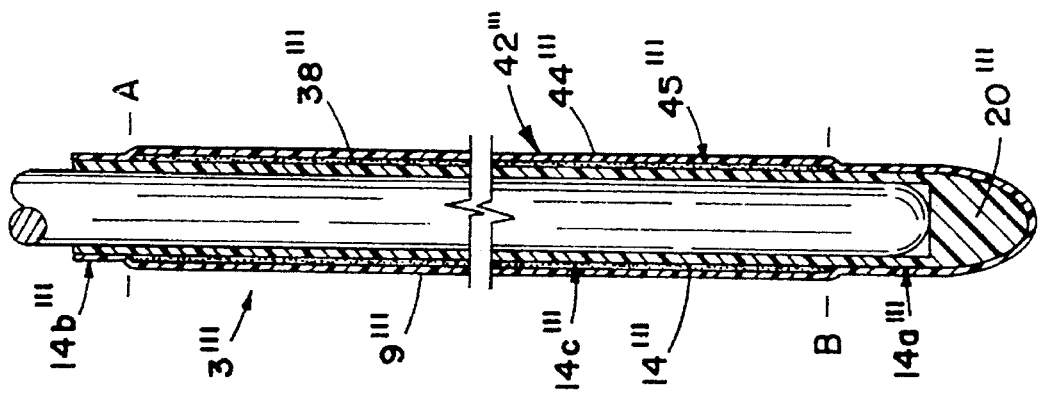
FIG. 49 is a transverse schematic view in partial cross-section of an elongated catheter in accordance with the present invention which is made from the alternate intermediate tube shown in FIG. 48.

Referring now generally to the drawings, and specifically to the cannulas and catheters 4, 5 shown in FIGS. 15–18; 4', 5' shown in FIGS. 36–38; 4" shown in FIGS. 39 and 40; and 4''' shown in FIGS. 48 and 49, the present invention provides cannulas and/or catheters 4, 5 having an outer bactericide release layer 61 which is capable of a sustained release or diffusion of an antibacterial agent into aqueous environments proximate the outer bactericide release layer 61. The outer bactericide release layer 61 is preferably a cured silicon rubber polymeric matrix. Impregnated within the cured silicon rubber polymeric matrix is a bacterial agent. This bacterial agent is nitrofuran compound having the formula:

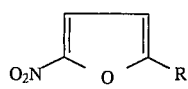

where R is a carbon-containing organic moiety, such as that disclosed, for example, in K. Miura et al., entitled "The Nitrofurans," in *Progress in Medicinal Chemistry* (Vol. 5), pp. 320–381, (G. P. Ellis & G. B. West (eds.), Plenum Press, New York, N.Y. (1967), the disclosure of which is incorporated by reference herein. The preferred nitrofurans are nitrofurans which are soluble in water and have antibacterial activity in aqueous environments.

Preferred nitrofuran compounds include nitrofurantoin, nitrofurazone, nidroxyzone, nifuradene, furazolidone, furaltidone, nifuroxime, nihydrazone, nitrovin, nifurpirinol, nifurprazine, nifuraldezone, nifuratel, nifuroxazide, urfadyn, nifurtimox, triafur, nifurtoinol, nifurzide, nifurfoline, nifuroquine, and derivatives of the same, and other like nitrofurans which are both soluble in water and possess antibacterial activity. References to each of the above cited nitrofuran compounds may be found in the Merck Index, specifically the ninth edition (1976) and the eleventh edition (1989) thereof, published by Merck & Co., Inc., Rahway, N.J., the disclosures of which are each incorporated herein by reference. It will be appreciated that the most preferred nitrofuran compounds are nitrofuran compounds which are medically acceptable for topical use, preferably topical use for mucosal surfaces.

Preferably, the nitrofuran compounds have a solubility of about 0.2% by weight or less in water at a pH of about 6 and temperature of about 25° C. More preferably, the nitrofuran compounds have a solubility in water of about 0.2 to about 0.001% by weight in water at a pH of about 6 and a temperature of about 25° C. Even more preferably, the solubility of the nitrofuran compound under these conditions is about 0.1% by weight or less. It will be appreciated that it is important to have an antibacterial agent which is effective to prevent the proliferation and colonization of bacteria within aqueous systems, and that it is also important to have an antibacterial agent which is not so soluble in aqueous systems that it will immediately diffuse out of the polymeric matrix within which it is incorporated. These characteristics are important in order to provide a sustained release of the antibacterial agent into these aqueous systems so as to provide for long-term antibacterial activity. It will also be appreciated that the rapid release or diffusion of the antibacterial agent into an aqueous environment in contact with the outer bactericide release layer 61 will also result in irregularities in the surface of the catheter or cannula 4, 5 which may irritate adjacent tissues within the patient's urinary tract.

It will be further appreciated that it is important that the outer surface of the outer bactericide release layer 61 is smooth so as to minimize the incidence of irritation to the tissues of the urinary tract. In order to provide a smoother outer surface, it is important to minimize the particle size of the finely divided nitrofuran compound particles incorporated into the outer bactericide release layer 61. The mean particle diameter of the nitrofuran compound particles is preferably about 200 microns or less, more preferably about 150 microns or less, and even more preferably about 100 microns or less. The size of the mean particle diameter is preferably controlled by filtering the larger particles out of the mixture used to coat the intermediate tubes used to make the finished catheters or cannulas 4, 5.

In preferred embodiments of the present invention, the outer bactericide release layer 61 includes silicone fluid which is incorporated therein to provide for more rapid diffusion of the antibacterial agent upon exposure to aqueous medium. It is believed, but not relied upon, that the silicone fluid allows the cured silicone polymeric matrix to provide for greater diffusion of aqueous media into and out of the polymeric matrix. In addition, the silicone fluid is desirable because it provides a softer, more pliable polymeric matrix which is also easier to elongate. It is further believed that the incorporation of the silicone fluid along with the minimization of the mean particle diameter of the nitrofuran compound particles cooperate to maximize the smoothness of the outer surface of the outer bactericide release layer 16, and to maximize the structural integrity, softness and stretchability of the release layer 61. The structural integrity is also important so that the amount of the antibacterial agent incorporated into the release layer 61 can be maximized. It will be appreciated that the greater the structural integrity of the polymeric matrix, the less the matrix will break down and disintegrate. If the release layer attached to the catheter or cannula 4, 5 disintegrates or flakes off for lack of better bonding, the product will be unacceptable in the marketplace. Although it is believed that the most important factor in this regard is the small particle size, it is also important to incorporate some silicone fluid to soften the polymeric matrix and allow it to be more stretchable, thereby minimizing the rigidity of the polymeric matrix. Although it is possible to use nitrofuran compound particles of virtually any size, it will be appreciated that a mean particle diameter of less than about 500 microns will be preferred and that even smaller mean particle diameters such as about 400 microns or less, preferably about 300 microns or less, more preferably about 200 microns or less, will be more preferred in order to be able to incorporate more of the drug into the polymeric matrix and still have a soft and pliable polymeric matrix and a smooth outer surface so as to provide commercially acceptable products. In preferred embodiments of the present invention, the outer bactericide release layer 61 preferably includes about 2–80% by weight, more preferably about 5–70% by weight, even preferably about 10–60% by weight, and most preferably about 15–55% by weight of the nitrofuran compound in the present invention, and outer bactericide release layer will include an anti-inflammatory agent in amounts similar to the amounts recited herein for the nitrofuran compound. The preferred anti-inflammatory agents are water soluble, anti-inflammatory agents such as hydrocortisone, hydrocortisone acetate, hydrocortisone phosphate, hydrocortisone hemisuccinate sodium salt, hydrocortisone tebutate, and the like. In this regard, it will be appreciated that any therapeutically acceptable, water soluble anti-inflammatory agent may be used in the present invention in order to reduce inflammation of the tissues adjacent to the present catheter or cannula 4, 5 when inserted in a human body. In an alternate embodiment of the present invention, the hydrocortisone compound has a solubility in water of less than about 0.1% by weight.

In order to provide long-term sustained release antibacterial activity, the present catheter or cannula 4, 5 preferably provides an outer bactericide release layer 61 having a smoother outer surface such that it minimizes irritation to adjacent tissues. This release layer 61 preferably includes about 10–60% by weight of a preferred nitrofuran compound or a combination thereof having a mean particle diameter of 200 microns or less. Preferably, the catheter or cannula 4, 5 of the present invention provides a potential for sustained release of the antibacterial agent incorporated in the outer bactericide release layer 61 for a period of at least about two weeks, preferably at least about three weeks, more preferably at least about four weeks, and even more preferably about five weeks. In further embodiments, the antibacterial agent is released for periods of at least about six weeks, seven weeks, eight weeks, or more, depending upon the amount of the solid nitrofuran compound which is incorporated into the release layer 61 and the solubility thereof in water. It will be appreciated, however, that although it is desirable to incorporate a large amount of the nitrofuran compound into the release layer 61, it is also important to retain the elongation characteristics and smoothness which is generally available to cellastic membranes used on similar catheters or cannulas. It will be appreciated that the rate of release of the nitrofuran compound into the surrounding aqueous environment is dependent on the rate of fluid exchange. It has been observed that 3 milliliters of fluid exchange generally occurs within an average female urinary tract every 24 hours. Because the antibacterial agent concentration in the fluid adjacent to the release layer 61 will generally release a point of equilibrium with the antibacterial agent within the release layer 61, the diffusion rate of the antibacterial agent out of the release layer 61 will be slowed as the concentration reaches maximum solubility for the particular nitrofuran compound incorporated into the release layer 61. As additional fluid passes into the urinary tract and dilutes the fluid already present or washes the fluid out, the diffusion rate will increase. In this way, the present invention is designed to attempt to maintain a concentration of the antibacterial agent in the aqueous fluids within the urethra at a level generally commensurate with the maximum solubility of the antibacterial agent. It will be appreciated, however, that this will not always be the case. Therefore, it is also important to provide a burst of antibacterial agent in the urethra upon insertion of the catheter or cannula 4, 5 so as to immediately eliminate the presence of viable bacterial therein. This is accomplished when a Foley catheter 4, 5 such as that shown in FIGS. 15–18 is inserted into the urinary tract and the expandable balloon portion 58 is expanded, thereby stretching the release layer 61 proximate the expandable balloon portion 58. This increases the diffusion rate of the antibacterial agent from the release layer 61 proximate the expandable balloon portion 58 and allows for a sudden increase in the concentration of the antibacterial agent in the fluids adjacent to the expandable balloon portion 58.

In the preferred embodiment, nitrofurazone is the nitrofuran compound of choice. When using nitrofurazone, it is desirable to maintain a nitrofurazone concentration in aqueous fluids adjacent to the catheter at about 0.02% by weight in order to minimize and preferably eliminate bacterial proliferation within the urinary tract. It will be appreciated that nitrofurazone is desirable, not only because of its limited solubility in water, but also because of its broad antibacterial activity in respect to both Gram positive and Gram negative bacteria which commonly infect the bladder and the urinary tract. It is also desirable because of its bright yellow color, which provides an attractive product for commercial presentation. In addition, nitrofurazone appears to stand up rather well to high temperatures used to cure the silicone rubber within the release layer 61 during processing. Although silicone rubber matrices created from silicone rubber vulcanizing systems which do not require heat, such as RTV systems and the like, may be cured at ambient temperatures, the heat cured silicone rubber matrices are preferred.

In preferred embodiments, a silicone rubber/nitrofurazone dispersion or mixture is prepared as follows: 100 grams of nitrofurazone powder is wetted with approximately 10 fluid ounces of 1,1,1-trichloroethane (Hydrite Chemical Co., LaCrosse, Wis.). This mixture is agitated vigorously. In a separate container, 100 grams of uncured silicone rubber (2 parts platinum cure system, ½ part A and ½ part B (Dow Corning, Midland, Mich.)) is dispersed with about 20 grams of silicone fluid (360 fluid, 20 centistoke (Dow Corning, Midland, Mich.)) in a ratio of 5 parts to 1 in approximately 10 fluid ounces of 1,1,1-trichloroethane (Hydrite Chemical Co., LaCrosse, Wis.). Another 30 fluid ounces of 1,1,1 trichloroethane is added to the nitrofurazone/trichloroethane mixture, and agitated continuously. The nitrofurazone/trichloroethane mixture is passed through a filter to remove the larger nitrofurazone particles. Preferably, two 6-inch cone-shaped filters from TUFCO (medium mesh) are used back-to-back (one inside the other) to filter the nitrofurazone/trichloroethane mixture. The filtering step is repeated three or four times to remove the larger, oversized particles of nitrofurazone which will not pass through the medium mesh TUFCO filters. When the larger particles have been removed, the nitrofurazone/trichloroethane mixture or dispersion is combined with the silicone rubber dispersion and agitated constantly. Preferably, the fluid mixture of the solid nitrofurazone particles in the silicone rubber dispersion is allowed to settle just prior to dipping to form the release layer 61 on the outer surface of the overcoat layer 44 as further discussed herein below. It will be appreciated that the dispersion may be pumped through a single filter or a series of filters designed to provide a nitrofurazone dispersion having a precise mean particle diameter.

Referring now more specifically to the drawings, and specifically to FIGS. 1 and 2, the first step in making a balloon catheter in accordance with the present invention is providing a double lumen tube 2, which is preferably extruded and made of silicone rubber. It will be appreciated, however, that the double lumen tube can be made by any known process which yields a double lumen tube. It will be further appreciated that the tube can be made of any resilient polymeric material, preferably a biocompatible polymeric material which can be inserted into a human body cavity. The double lumen tube 2 includes a smaller capillary lumen 6 and a larger fluid conduit lumen 8.

Referring now also to FIGS. 3 and 4, after the double lumen tube is cut to a desired size, a capillary lumen access opening 12 is created in an outer surface 14 of the double lumen tube 2. The capillary lumen access opening 12 communicates with the capillary lumen 6.

Referring now also to FIGS. 5–7, an intermediate tube 3 is subsequently prepared from the double lumen tube 2 shown in FIG. 3. In the first step of this process, a measured amount of a polymeric bonding composition, preferably uncured silicone rubber or another suitable polymeric bonding material, is injected into the capillary lumen 6 from the distal end 16 of the double lumen tube 2, so that the capillary lumen 6 is filled with a polymeric fill material 18 up to a point just below the capillary lumen access opening 12. A tip 20, preferably a rounded silicone rubber tip, is then affixed to the distal end 16 of the tube 2 to complete the formation of the intermediate tube 3 shown in FIG. 7. In a preferred method, the distal end 16 of the tube 2 inserted into a molding apparatus (not shown) designed to mold a tip 20 on the end of the tube 2.

Referring now also to FIGS. 7–16 and 19, a preferred process of the present invention involves securing a plurality of intermediate tubes 3, like the intermediate 3 shown in FIG. 7, to a rack or pallet 24. The rack or pallet 24 will include a plurality of support rods 26, each equipped with a retaining clip 28. The intermediate tubes 3 are secured on the support rods 26 by engaging individual support rods 26 in the larger of the two lumens, called the fluid conduit lumen 8, and sliding the intermediate tubes 3 up over the support rods 26 until the proximal ends 30 of the intermediate tubes 3 abut against the base of the retaining clips 28 or, preferably, the tip 20 of each of the intermediate tubes 3 fits snugly against the distal tip of each of the support rods 26, as shown in FIGS. 9 and 10. Although not shown, it is believed that the intermediate tubes 3 can be secured on the support rods 26 without the aid of the retaining clips 28. This is because the preferred extruded double lumen tubes 2 used to make the intermediate tubes 3 generally have a slight bend in one direction or another when they are hung. This results in a slight bend in the intermediate tubes 3 that permits the intermediate tube 3 to be secured on a support rod 26 without the aid of a clip 28. Because of the nature of the polymeric materials generally used to make the intermediate tubes 3, they also have a tendency to cling to other surfaces and to offer resistance to movement of a surface along a surface of this material.

When the intermediate tubes 3 have been secured on the support rods 26, the pallet 24 can be transferred from place to place, and the intermediate tubes 3 on the pallet 24 can be dipped in a series of baths (see FIG. 19) prepared to accomplish a series of process steps. In the preferred method of the present invention, the intermediate tube 3 is made nearly entirely of silicone rubber and is secured upon a support rod 26 made of spring steel. The tip 20 and the fill material 18 of the intermediate tube 3 shown in FIG. 7 are made of the same material (silicone rubber) as the double lumen tube 2. Therefore, the tip 20 and the fill material 18 form integral portions of the intermediate tube 3, which is shown in FIGS. 9–16 as an integral polymeric unit made of a single material.

The first step in the automated coating or dipping process of forming the balloon portion 32 of the balloon catheter 4 (shown in FIG. 13), after the intermediate tubes 3 are secured to the pallet 24, is to coat the intermediate tubes 3 with a bond preventing agent, preferably a removable bond preventing agent. Preferably this is accomplished by dipping each of the tubes 3 on the pallet 24 simultaneously into a first dip tank 33 containing a bath 33a of a removable bond preventing agent, preferably a material which forms a semi-solid film on surfaces when cooled on contact followed by an opportunity for drying. Examples of such materials include petroleum jelly or petrolatum, other oil base substances which form a semi-solid upon cooling to room temperature, liquid soaps which dry to form a semi-solid, aqueous soap or detergent solutions, aqueous or oil based film forming solids emulsions, and the like. In one embodiment described herein, hot petrolatum is used, and in another, a liquid soap is used, preferably Liquid Ivory Soap from Proctor & Gamble, Cincinnati, Ohio.

When the intermediate tubes 3 are removed from this first bath 33a of removable bond preventing agent, the agent adheres to the outer surface 14 of the intermediate tube 3, and enters the capillary lumen access opening 12 and runs up into the capillary lumen 6. In one embodiment the agent is petrolatum, which is heated to about 140°–160° F., preferably about 150° F. At these temperatures, the petrolatum will run up into the capillary lumen 6 through the capillary lumen access opening 12 with the assistance of the "capillary effect", which draws the fluid into the capillary lumen 6 to the level of the petrolatum in the first tank 33. As the intermediate tubes 3 are withdrawn from the hot petrolatum, petrolatum on each tube cools and solidifies to form a semi-solid coating 38 on the outer surface 14 and a semi-solid filling 34 in the capillary lumen 6 and the capillary lumen access opening 12 which cooperate to plug the capillary lumen access opening 12. In an alternate embodiment, the bond preventing agent in the first tank 33 is liquid soap at room temperature (about 62°–74°). When the tubes 3 are withdrawn from the first dip tank 33, the liquid soap forms of semi-solid just as the hot petrolatum did as it cooled. Although both of these bond preventing agents are effective, there is some advantage to using the soap because it does not require the added expense for heating. Furthermore, it is believed soap is easier to remove from the capillary lumen 6 and the balloon cavity 54.

After the intermediate tubes 3 are coated and the capillary lumen access openings 12 are plugged simultaneously with bond preventing agent in this manner (see FIG. 10), the tubes 3 are then dipped in a series of dip tanks (see FIG. 19) provided to remove the bond preventing agent from a portion 14a of the outer surface 14 below the dashed line designated B. After this portion 14a of the outer surface 14 is substantially stripped of any residue of the bond preventing agent, the intermediate tubes 3, now partially coated with bond preventing agent between the dashed lines designated A and B as shown in FIG. 12, are dipped in a polymeric bonding composition, preferably silicone rubber, in a step or steps provided to coat the intermediate tube 3 to create the balloon catheter 4 shown in FIGS. 13–14. In the preferred methods, the intermediate tube 3 is dipped in silicone rubber in two or more successive dipping steps so that the resulting overcoat layer includes at least an underlying and an overlying layer, 43 and 44 respectively, which form an integral part of the balloon catheter 4 and are bonded together and to the outer surface 14 in the portions thereof, 14a and 14b, which are located below the dashed line designated B and above the dashed line designated A, respectively. The portion 14b above line A was not coated prior to the final dipping steps designed to provide the overcoat layer 42, and the portion 14a below line B was stripped of its coating prior to those steps. The balloon catheter 4 is then dipped in the silicone rubber/nitrfurazone fluid mixture described hereinabove to form an outer bactericide release layer 61 shown in FIGS. 15 and 16.

In subsequent steps, the proximal end 30 of the balloon catheter 4 is secured to an end piece 46 to form a completed Foley catheter 5 (shown in FIG. 17). The end piece 46 can include a cap 48 for closing a proximal end access opening 49 to the fluid conduit lumen 8 and can be equipped with a luer valve 50 for engagement in and closure of the proximal capillary lumen access upper opening 52 communicating with the capillary lumen 6. Prior to the attachment of the end piece 46 to the balloon catheter 4 to form the completed Foley catheter 5, the completed balloon catheter 4 is preferably allowed to air dry to permit solvents in the outer bactericide release layer 61 to evaporate and is subsequently cured at an elevated temperature. Care is taken to keep the curing temperature below the boiling temperatures of the solvent so as to prevent unsightly bubbling of the solvent within the overcoat layer 42 or the outer bactericide release layer 61. Because the overcoat layer 42 and the outer bactericide release layer 61 are made of the same polymeric bonding composition, even though each respective layer 42, 61 may be created in a plurality of dipping steps, they are represented in FIGS. 15–18 as single layers 42, 61.

The completed Foley catheter 5 also includes a fluid conduit access opening 56 in an exterior surface 63 of the completed Foley catheter 5. The fluid conduit access opening 56 communicates with the fluid conduit lumen 8. In preferred embodiments, the access opening 56 is punched into the catheter 5 following the curing steps. Preferably, two access openings 56, one on either side of the catheter 5 (second access opening 56 not shown) are punched into the catheter 5. In an alternate embodiment (not shown), the access opening 56 is created before the intermediate tube 4 is dipped in the silicone bactericide coating mixture (silicone/nitrofuran compound fluid mixture). In this embodiment, an inner surface layer (not shown), incorporating the bactericide agent 15 is created along an inside of the fluid conduit lumen 8.

In preferred methods in accordance with the present invention, the end piece 46 is made by a process of injection molding. Preferably, the proximal end 30 of the balloon catheter 4 is inserted into the injection molding apparatus after the overcoat layer 42 and the release layer 61 have been cured. The polymeric bonding composition, preferably silicone rubber, is then injected into the mold (not shown) and the end piece 46 is molded onto the proximal end 30 of the balloon catheter 4 to make the completed Foley catheter 5 shown in FIG. 17. Following further drying curing steps where deemed necessary given the type of polymeric bonding composition or compositions used to make the completed Foley catheter 5, the completed catheter 5 is tested to see if it is functional and if it has any leaks. This testing can be done before or after the fluid conduit access opening 56 is created in the exterior surface 62 to communicate with the fluid conduit lumen 8. Care is taken during such testing to avoid any needless exposure of the release layer 61 or any other nitrofuran impregnated natrices to aqueous environments.

In order to test the integrity of the completed catheter 5, prior to engaging the plug 50 in the proximal capillary lumen access opening 52 in the end piece 46, the proximal capillary lumen access opening 52 is slipped over a hot water nozzle (not shown), and a measured amount of a hot aqueous solution, preferably water or water containing a trace of surfactant, at a temperature of between about 120°–160° F., preferably about 140° F., is pumped into the capillary lumen 6 from a standard hot water heater (not shown) by a commercially available water pump (not shown) such that the balloon portion 58 is expanded. The balloon portion 58 of the overcoat layer 42 is the portion of the overcoat layer 42 which is not bonded to the outer surface 14 of the intermediate tube 3. The balloon portion 58 of the overcoat layer 42 cooperates with the portion 14c of the outer surface 14 which remained coated with the bond preventing agent prior to the step of dipping the intermediate tube 3 in the polymeric bonding composition, to define a balloon cavity 54. The balloon cavity 54 communicates with the capillary lumen 6 via the capillary lumen access opening 12. When the hot water solution is pumped or injected into the capillary access lumen 6 to test the completed catheter 5 and the balloon portion 58, the balloon portion 58 and the balloon cavity 54 are expanded. If there is a significant lack of integrity in the balloon portion 58 it will be exposed when the water is introduced in this manner. In addition to testing the balloon portion 58, the water solution will also remove the remaining bond preventing agent in the balloon lumen 54 and the capillary lumen 6 when it is removed. Although some of the bond preventing agent may come out of the capillary lumen 6 via the proximal capillary lumen access opening 52 during the step of curing the overcoat layer 42, the hot aqueous solution is generally believed to remove most of the bond preventing agent, although a residue may remain.

Following the preliminary test, which relies on a visual observation to determine whether there is any lack of integrity, a further test is used to obtain further assurance that there are no leaks in the balloon portion 58. This further test is accomplished by engaging the proximal capillary lumen accessing opening 52 to the nozzle of a commercially available leak tester (not shown). One such device is a Model No. 6510 Caps Tester from Caps Himmelstein (Hoffman Estates, Ill. 60195). Once the completed catheter 5 is tightly secured over the nozzle, an electrical switch, such as a hand switch or, preferably, a foot pedal, is used to release a measured blast of air into the capillary lumen 6. When the air is introduced into the capillary lumen 6 it also enters the balloon cavity 54 via the capillary lumen access opening 12 and inflates the balloon portion 58 and, thereby, expands the balloon cavity 54. The leak tester is designed to sense any loss of pressure once the balloon portion 58 is inflated, and will given an indication, therefore, if there are any measurable leaks. After this test is completed, the completed catheters 5 that have passed all tests, are then packaged, preferably in a material which breathes such as Tyvek™ (from DuPont), and boxed. The boxes are then sterilized with ETO (ethylene oxide) and then stored for shipment.

In the Applicants' use of the preferred methods of the present invention, balloon fabrication is almost completely automated. Entire sets of balloon catheters 4 are manufactured simultaneously. The preferred pallet 24 has 400 spring steel support rods 26 attached to a pallet in 20 rows of 20 rods, wherein each of the rods 26 is about 1 inch from each adjacent rod. Double lumen tubing (not shown) is preferably made by an extrusion process which is known to those of skill in the art. The tubes 2 are cut to length as the tubing leaves the extruder (not shown). An opening 12 is created in the outer surface 14, preferably with a hollow drill bit or tube (not shown), so as to communicate with the capillary lumen 6. The distal portion 6a of the capillary lumen 6, located between the distal end 16 of the tube 2 and the capillary lumen access opening 12, is injected with a measured amount of a polymeric bonding composition, preferably silicone rubber, so that the distal portion 6a is filled and sealed. A rounded tip 20 is preferably formed at the distal end 16 of the double lumen tube 2 by inserting the tube 2 in a molding device (not shown).

In one embodiment of the present method, 400 of the intermediate tubes 3 are then mounted vertically on rigid spring steel support rods 26 on a pallet 24 in the manner previously described. The pallet 24 is then moved via a transporting mechanism 22 (see FIG. 19) over a series of dip tanks as follows in one of these embodiments:

(A) The pallet 24 is stopped over a first tank 33, which contains white USP petrolatum heated to about 67° C. (about 150° F.). The tank is raised so as to immerse the intermediate tubes 3 into the petrolatum to such a depth that the petrolatum reaches the proximal end of the desired balloon location. The dip tank 33 is then lowered and a portion of the outer surface 14 of the intermediate tubes 3 are coated with petrolatum. This portion extends from the point at which the proximal end of the balloon portion 58 will begin to the distal end of the tip 20 of the intermediate tube 3.

(B) The pallet 24 is then automatically advanced and stopped over a second dip tank 35 which contains white USP petrolatum heated to about 120° C. (about 250° F.). The second dip tank 35 is raised so as to immerse the intermediate tubes 3 into the super-heated petrolatum so that the super-heated petrolatum comes into contact with the petrolatum coating on outer surface 14 of the intermediate tube 3 from the prior dipping step up to a location where a distal end of the balloon portion 58 will end. The second dip tank 35 is then lowered. This dipping step causes the coating of petrolatum from the prior dipping step to be largely removed from a portion 14a of the outer surface 14 of the intermediate tube 3 from a location where the distal end of the balloon lumen 54 will be located (designated by dashed line B) to the distal end 20a of the tip 20 of the intermediate tube 3. Some residual petrolatum may remain on the outer surface 14 of the intermediate tube 3 in this portion 14a of the outer surface 14. However, most of the petrolatum is removed.

(C) The pallet 24 is then automatically advanced and stopped over a third dip tank 37 containing mineral spirits heated to about 200° F. The third dip tank 37 is then raised so as to immerse the intermediate tubes 3 into the mineral spirits to the same depth as they were immersed in the super-heated petrolatum in the second dip tank 35. The tank 37 is then lowered and all but a trace amount of the petrolatum is removed from the portion 14a of the outer surface 14 below the portion 14c of the outer surface 14, which will eventually be proximate the balloon lumen 54.

(D) The pallet 24 is then automatically advanced and stopped over a fourth dip tank 39 containing a volatile organic solvent such as toluene, trichloromethane or the like. The fourth tank 39 is then raised to immerse the intermediate catheters 3 to the same depth as previously immersed in the second and third tanks 35 and 37, thereby removing essentially all traces of the petrolatum from this portion 14a of the outer surface 14. The intermediate catheter tube 3 now has a band 38 of semi-solid petrolatum located around the axial circumference of the intermediate tube 3 in the location where the balloon cavity 54 will be created. The petrolatum not only coats the portion 14c of the outer surface 14 located in this area, but also fills a portion of the capillary lumen 6 and plugs the capillary lumen access opening 12, which will eventually be used to inflate the balloon portion 58 of the completed Foley catheter 5.

(E) The pallet 24 is then lowered and automatically advanced to a fifth dip tank 41 containing a low-solids hexamethyl disiloxane or toluene silicone rubber solution which is effective to minimize any disruption of the integrity of the petrolatum coating 38 remaining on the intermediate tube 3 proximate the portion 14c of the outer surface 14 where the balloon lumen 54 will be created during subsequent dipping steps. The fifth tank 41 is then raised to immerse essentially the entire length of the intermediate tube 3 in the solution. This step can be subsequently repeated at intervals, preferably allowing time for significant solvent evaporation, either in the same tank or in a subsequent tank containing a greater concentration of silicone rubber, until the overcoat layer 42 and the balloon portion 58 of the overcoat layer 42 have a desired balloon thickness. The preferred thickness over the overcoat layer 42 and the balloon portion 58 is 17.5 thousandths of an inch (plus or minus 2.5 thousandths of an inch). The tank 41 is then lowered, and the overcoat layer 42 is allowed to dry and the solvent is allowed to evaporate for about 15 minutes, preferably about 30 minutes, even more preferably about an hour.

(F) The pallet 24 is advanced to a sixth dip tank 43 containing a silicone rubber/nitrofuran compound mixture or dispersion 17, and the tubes 3 are completely immersed again. The tank 43 is lowered. The pallet is then advanced through a drying area where solvents are allowed to evaporate, and then through a heat cure step, where the balloon catheters 4 formed by this process are cured at a temperature just below the boiling point of any solvent used in any of the silicone rubber dip solutions for an hour or two. For toluene this temperature is about 200° F.

(G) After the heat cure, the balloon catheters 4 are allowed to cool and are then removed from the support rods 26. The proximal ends 30 of each of the balloon catheters 4 is then inserted into an injection molding apparatus (not shown), which forms the end piece 46 of the completed Foley catheter 5.

(H) The completed Foley catheters 5 are then finished by punching a fluid conduit access opening 56 in the exterior surface 62 such that it communicates with the fluid conduit lumen 8 in a location below or distal to the balloon portion 58.

Figure 20A:
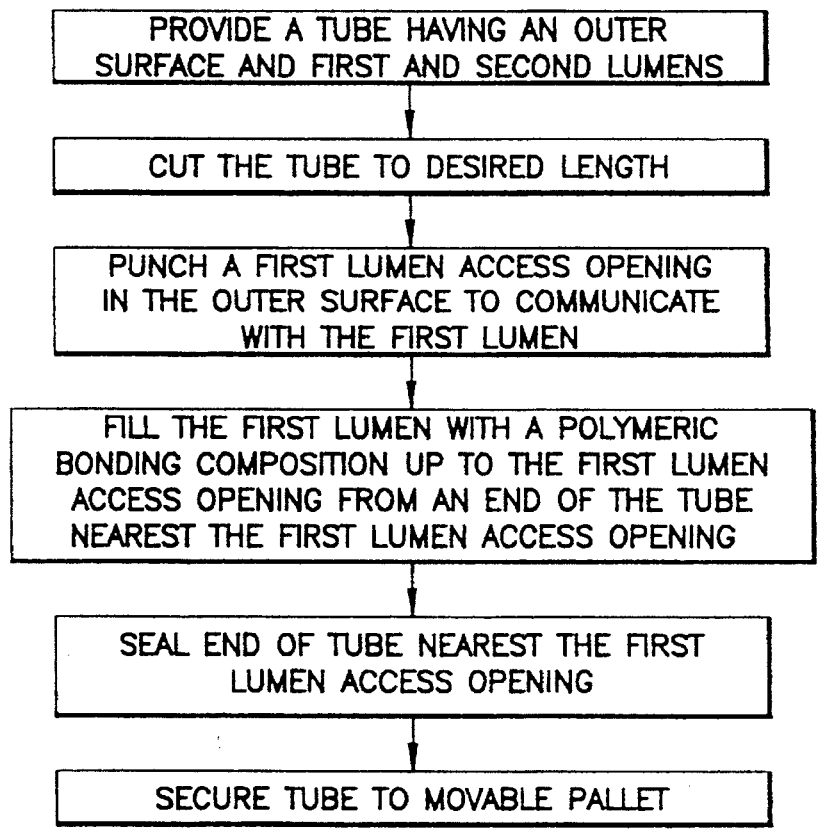
FIG. 20a, 20b and 20c are flow charts representing certain steps in accordance with the present invention.
Figure 20B:
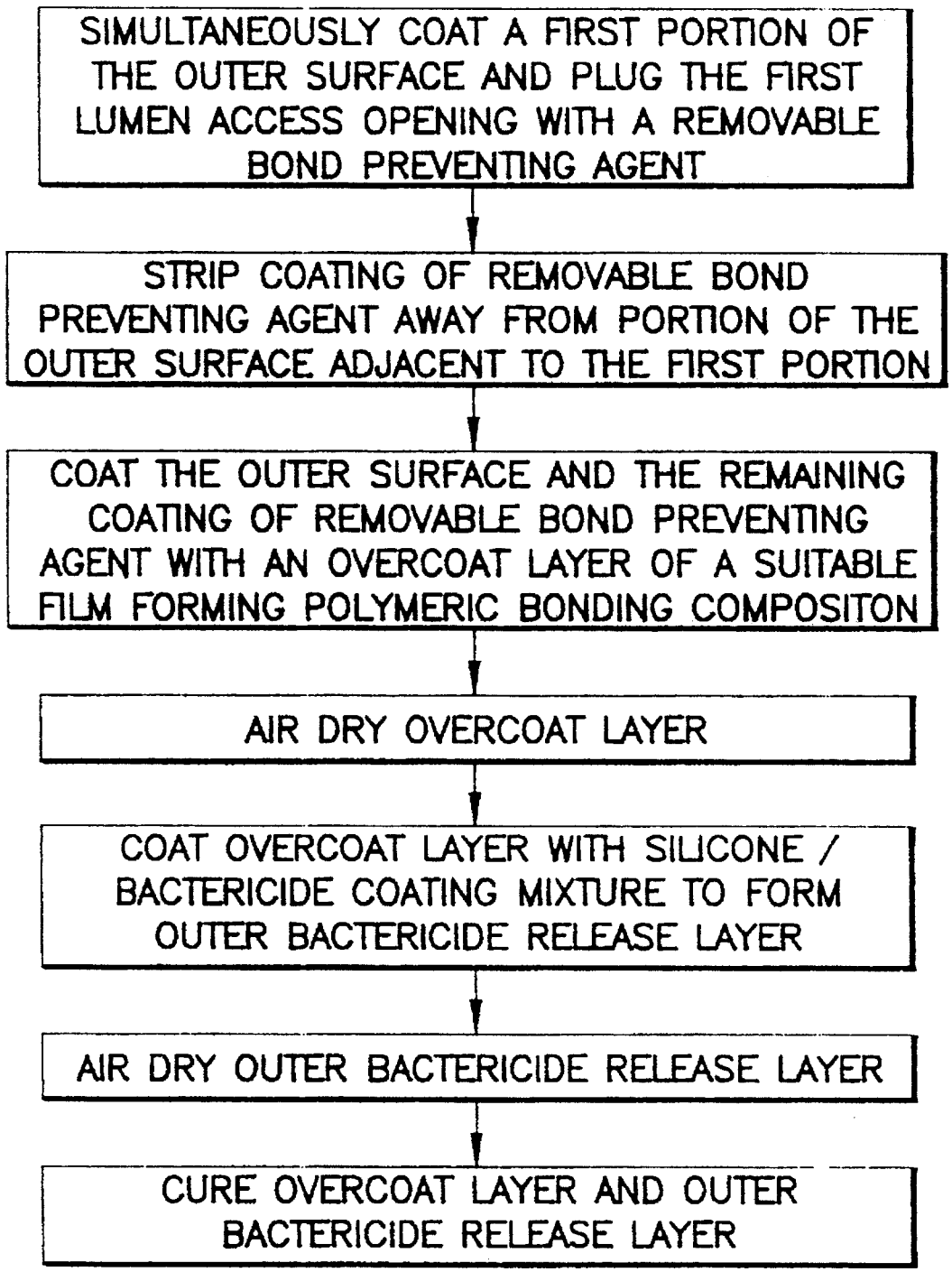
Figure 20C:
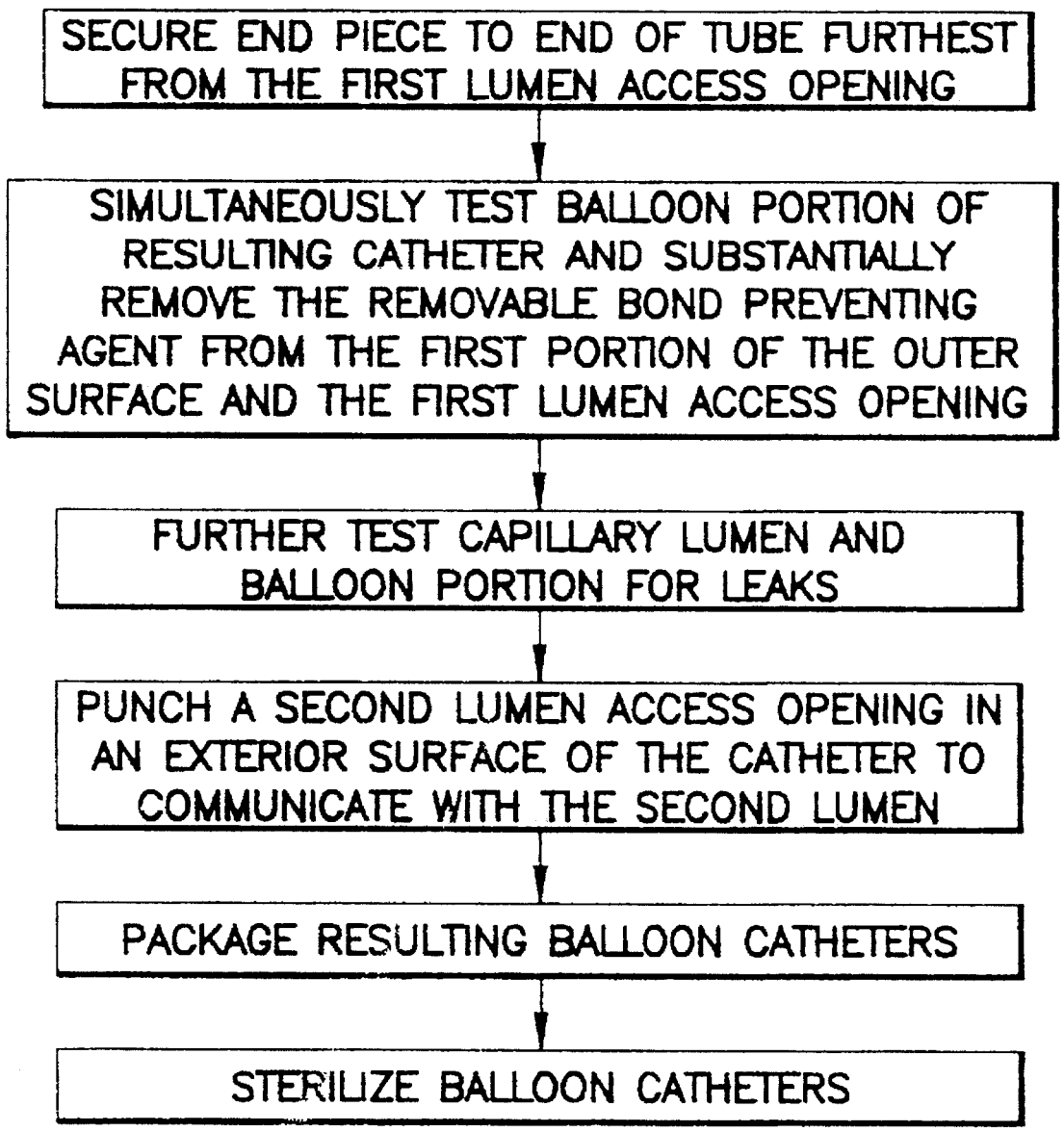

(I) The completed Foley catheters 5 are then sent through the test sequence described hereinabove, during which the balloon portion 58 of each completed Foley catheter 5 is inflated and the petrolatum band 38 within the balloon cavity 54 is largely removed. Referring now to FIGS. 20a, 20b and 20c, the present invention provides a method of making balloon catheters including the following steps:

(A) Providing a tube having an outer surface and first and second lumens;

(B) Cutting the tube to a desired length;

(C) Creating a first lumen access opening in the outer surface to communicate with the first lumen;

(D) Filling the first lumen with a polymeric bonding composition up to the first lumen access opening from an end nearest the first lumen access opening;

(E) Sealing the end of the tube nearest the first lumen access opening; and (F) Securing the tube to a movable pallet.

These steps are followed by the following steps:

(A) Simultaneously coating a first portion of the outer surface and plugging the first lumen access opening with a removable bond preventing agent;

(B) Stripping the coating of removable bond preventing agent away from a portion of the outer surface adjacent to the first portion;

(C) Coating the outer surface and the remaining coating of removable bond preventing agent with an overcoat layer of a suitable film forming polymeric bonding composition;

(D) Coating the overcoat layer with a silicone rubber/ bactericide coating mixture to form an outer bactericide release layer;

(E) Air drying outer bactericide release layer; and (F) Curing the overcoat layer and the outer bactericide release layer.

Following those steps, methods of the present invention include the following steps:

(A) Securing an end piece to the end of the tube furthest from the first lumen access opening;

(B) Simultaneously testing the balloon portion of the resulting catheter and substantially removing the removable preventing bond agent from the first portion of the outer surface and the first lumen access opening;

(C) Further testing the catheter capillary lumen and the balloon portion for leaks;

(D) Punching a second lumen access opening in an exterior surface of the catheter to communicate with the second lumen;

(E) Packaging the resulting balloon catheters; and (F) Sterilizing the balloon catheters.

In preferred embodiment of the present invention following the securing of a plurality of intermediate tubes 3 to the transportable pallet 24, balloon catheters are produced as follows:

(A) The pallet 24 is stopped over a first tank 33, which contains a liquid soap (Liquid Ivory Soap from Proctor & Gamble Co., Cincinnati, Ohio 45202). The soap is held at room temperature (between about 60°–80° F., preferably 65°–72° F.). The dip tank 33 is raised so as to immerse the intermediate tubes 3 into the liquid soap so that the soap coats the tubes 3 up to the dashed line designated by the letter A in FIG. 10. The dip tank 33 is then lowered and the liquid soap forms a semi-solid coating 38 on the outer surface 14 of each of the intermediate tubes extending from line A to the distal end of the tip 20 of the intermediate tubes 3.

(B) The pallet 24 is then automatically advanced and stopped over a second dip tank 35 which contains an aqueous solution containing a trace of a suitable wetting agent or surfactant. In a preferred embodiment, three gallons of water is mixed with two ounces of a suitable surfactant. The surfactant will generally be less than one percent of the total volume of the solution. The second dip tank 35 is then raised so as to immerse the intermediate tubes 3 in the aqueous fluid up to the dashed line designated by the letter B in FIGS. 10 and 12. The second dip tank 35 is then lowered and the semi-solid liquid soap coating the portion 14a of the outer surface 14 below the dashed line designated B is substantially removed.

(C) The pallet 24 is then automatically advanced and stopped over a third dip tank 37 containing water. The third dip tank 37 is then raised and the intermediate tubes are immersed in the water up to the line designated B as in the prior dipping step. The third dip tank 37 is then lowered and virtually all of the liquid soap is removed from the portion 14a of the outer surface 14 below the line designated B.

(D) The pallet 24 is then automatically advanced and stopped over a fourth dip tank 39 containing a low-solids hexamethyl disiloxane silicone rubber solution which is effective to minimize any disruption of the integrity of the liquid soap coating 38 remaining on each of the intermediate tubes proximate the portion 14c of the outer surface 14 where the balloon lumen will be created during subsequent dipping steps (the portion between the dashed lines designated A and B). The fourth tank 39 is then raised to immerse essentially the entire length of each of the intermediate tubes 3 in the silicone rubber solution. It will be appreciated that other organic solvents such as toluene, and the like may be substituted for the hexamethyl disiloxane solvent used in this example. It will also be appreciated that the dipping step can be repeated at subsequent intervals, preferably long enough to permit significant solvent evaporation (prior to any subsequent dipping), to add to the thickness of the overcoat layer 42 and the balloon portion 58 of the overcoat layer 42. Further steps, involving different solutions, can also follow.

(E) Once the fourth dip tank 39 is lowered, and the uncured silicone rubber, coating portions of the outer surface 14 as well as the coating of soap 38, is allowed to dry, the pallet 24 is advanced again to a fifth dip tank 41 preferably containing a different silicone rubber solution having a solids content which is higher than the solids content in the fourth dip tank 39. This step can be eliminated, but may be useful to add thickness if desired. The intermediate tubes are immersed again in the subsequent silicone rubber solution when the fifth dip tank 41 is raised. The fifth dip tank 41 is then lowered, and the silicone rubber coating the tubes 3 is allowed to dry.

(F) The pallet 24 is then automatically advanced again to a sixth dip tank 43 containing the silicone rubber/nitrofuran compound fluid mixture described hereinabove. The tubes can be dipped a second time after allowing about 10–15 minutes for drying. The sixth dip tank 43 is then lowered and the silicone rubber/nitrofuran compound coating the tubes 3 is allowed to dry for about 15 minutes.

(G) The pallet 24 is then advanced through a drying step followed by a heat cure step (air dried at 200° F. for 1 hour), and each completed balloon catheter 4 is then secured to an end piece, tested, provided with a fluid conduit access opening 56, packaged and sterilized.

The automated system that Applicants claim will permit completed Foley catheters 5 to be manufactured at the rate of about 1,600 catheters per hour. Because no handwork is involved, the catheters 5 produced will be consistent and of very high quality. The exterior surface 62 is smoother than hand-glued balloons, and the outside diameter of the balloon portion 58 is essentially identical to the outside diameter of other portions of the completed Foley catheters 5. In addition, by eliminating the hand labor involved in adhering the balloon portion 58 to the intermediate tube 3 in the manufacture of silicone rubber balloon catheters 4, by specifically eliminating the separate step of fabricating the balloon portion, which also requires hand labor, and by eliminating the significant impact on yield resulting from hand processing errors, the applicants' new process will permit direct production cost for silicone rubber balloon catheters of all types to be reduced by about 25–50% over the cost estimated for the prior art silicone rubber balloon catheters.

Referring now also to FIGS. 21–38, to FIGS. 21 and 22, the first step in making an alternate balloon catheter 4' in accordance with the present invention is providing a double lumen tube 2', which is preferably extruded and made of silicone rubber. It will be appreciated, however, that the double lumen tube 2' can be made by any known process which yields a double lumen tube 2'. It will be further appreciated that the tube 2' can be made of any resilient polymeric material, preferably a biocompatible polymeric material which can be inserted into a human body cavity. The double lumen tube 2' includes a smaller capillary lumen 6' and a larger fluid conduit lumen 8'. Referring specifically now also to FIGS. 23 and 24, after the double lumen tube 2' is cut to a desired size, a capillary lumen access opening 12' is created in an outer surface 14' of the double lumen tube 2'. The capillary lumen access opening 12' communicates with the capillary lumen 6'.

Referring specifically now also to FIGS. 25–27, an intermediate tube 3' is subsequently prepared from the double lumen tube 2' shown in FIG. 9. In the first step of this process, a measured amount of a polymeric bonding composition, preferably silicone rubber or another suitable polymeric bonding material, is injected into the capillary lumen 6' from the distal end 16' of the double lumen tube 2', so that the capillary lumen 6' is filled with a polymeric fill material 18' up to a point just below the capillary lumen access opening 12'. A tip 20', preferably a rounded silicone rubber tip, is then affixed to the distal end 16' of the tube 2' to complete the formation of the intermediate tube 3' shown in FIG. 13. In a preferred method, the distal end 16' of the tube 2' is inserted into a molding apparatus (not shown) designed to mold a tip 20' on the end of the tube 2'.

Referring now also to FIGS. 28–36 and 41, a preferred process of the present invention involves securing a plurality of intermediate tubes 3', like the intermediate tube 3' shown in FIG. 13, to a rack or pallet 24'. The rack or pallet 24' will include a plurality of support rods 26', each equipped with a retaining clip 28'. The intermediate tubes 3' are secured on the support rods 26' by engaging individual support rods 26' in the larger of the two lumens 8', called the fluid conduit lumen 8', and sliding the intermediate tubes 3' up over the support rods 26' until the proximal ends 30' of the intermediate tubes 3' abut against the base of the retaining clips 28' or, preferably, the tip 20' of each of the intermediate tubes 3' fits snugly against the distal tip 26a' of each of the support rods 26', as shown in FIGS. 29 and 30. Although not shown, it is believed that the intermediate tubes 3' can be secured on the support rods 26' without the aid of the retaining clips 28'. This is because the preferred extruded double lumen tubes 2' used to make the intermediate tubes 3' generally have a slight bend in one direction or another when they are hung. This results in a slight bend in the intermediate tubes 3' that permits the intermediate tube 3' to be secured on a support rod 26' without the aid of a clip 28'. Because of the nature of the polymeric materials generally used to make the intermediate tubes 3', they also have a tendency to cling to other surfaces and to offer resistance to movement of a surface along a surface of this material as do most polymeric tubes including those tubes 2 described hereinabove.

When the intermediate tubes 3' have been secured on the support rods 26', the pallet 24' can be transferred from place to place, and the intermediate tubes 3' on the pallet 24' can be dipped in a series of baths prepared to accomplish a series of process steps. In the preferred method of the present invention, the intermediate tube 3' is made entirely of silicone rubber and is secured upon a support rod 26' made of spring steel. The tip 20' and the fill material 18' of the intermediate tube 3' shown in FIG. 27 are made of the same material (silicone rubber) as the double lumen tube 2'. Therefore, the tip 20' and the fill material 18' preferably form integral portions of the intermediate tube 3', which is shown in FIGS. 29–36.

The first step in the automated coating or dipping process of forming the resilient sleeve 44' and the balloon portion 32' of the balloon catheter 4' (shown in FIG. 36), after the intermediate tubes 3' are secured to the pallet 24', is to coat the intermediate tubes 3' with a bond preventing lubricating agent or substance 38', preferably a removable bond preventing lubricating agent. Preferably this is accomplished by dipping each of the tubes 3' on the pallet 24', simultaneously into a first dip tank 33' containing a bath 33a' of a removable bond, preferably a material which forms a semi-solid film on surfaces when cooled on contact followed by an opportunity for drying. Examples of such materials include petroleum jelly or petrolatum, other oil base substances which form a semi-solid upon cooling to room temperature, liquid soaps which dry to form a semi-solid, aqueous soap or detergent solutions, aqueous or oil based film forming solids emulsions, and the like. In one embodiment described herein, hot petrolatum is used, and in another, a liquid soap is used, preferably Liquid Ivory Soap from Proctor & Gamble, Cincinnati, Ohio.

When the intermediate tubes 3' are removed from this first bath 33a' of removable bond preventing lubricating agent 38', the agent or substance 38' adheres to the outer surface 14' of the intermediate tube 3', and occupy the capillary lumen access opening 12' and the capillary lumen 6'. In one embodiment the agent is petrolatum, which is heated to about 140°–160° F., preferably about 150° F. At these temperatures, the petrolatum will run up into the capillary lumen 6' through the capillary lumen access opening 12' with the assistance of the "capillary effect", which draws the fluid into the capillary lumen 6' to the level of the petrolatum in the first tank 33'. As the intermediate tubes 3' are withdrawn from the hot petrolatum, petrolatum on each tube cools and solidifies to form a semi-solid coating 38' on the outer surface 14' and a semi-solid filling (not shown) in the capillary lumen 6' and the capillary lumen access opening 12' which cooperate to plug the capillary lumen access opening 12'. In an alternate embodiment, the bond preventing agent in the first tank 33' is liquid soap at room temperature (about 62°–74° F.). When the tubes 3 are withdrawn from the first dip tank 33, the liquid soap forms a semi-solid just as the hot petrolatum did as it cooled.

In the preferred method of the present invention, the intermediate tubes 3' are coated when they are dipped in a first bath 33a' which contains petrolatum which is maintained at a temperature effective to permit the petrolatum to coat the outer surface 14' of the tube while limiting the degree to which the petrolatum runs into the smaller lumen 6'. The petrolatum will run into the first lumen access opening 12', but, preferably, will not run very far into the smaller lumen 6'. The temperature of the petrolatum in the first tank 33' is preferably maintained at about 40°–80°, more preferably about 50°–70°, even more preferably about 55°–65°, and most preferably about 60° C. for this purpose. As shown in FIG. 29, the intermediate tube 3' is coated with the bond preventing lubricating agent 38' up to a location on the surface 14' of the intermediate tube 3' proximate the dashed line A shown in FIG. 29 by dipping the intermediate tube 3' into the first dip tank 33' up to that point.

Following this step, the outer surface 14' of the intermediate tube 3' is stripped of the bond preventing lubricating agent 38' up to a location proximate the dashed line designated B in FIGS. 29 and 30. This is preferably accomplished by one or more dipping steps in accordance with the methods for stripping particular lubricating agents as described hereinbelow. The intermediate tube is then preferably coated as shown in FIG. 30 between the locations proximate the dashed lines A and B. The intermediate tube 3' shown in FIG. 30 is then dipped in a subsequent dip tank holding a second bond preventing agent. In this step the liquid soap can be preferred, although petrolatum and other agents will also work. During this step, the intermediate tube 3' shown in FIG. 30 is dipped into the tank up to a point on the outer surface 14' of the intermediate tube 3' proximate the dashed line C so as to coat the portion of the intermediate tube 3' from the lowest portion of the tip 20' up to the location proximate the dashed line designated C. In preferred embodiments of the present invention, any of the bond preventing lubricating agents enumerated above may be used. Preferably, however, the bond preventing lubricating agent is hot petrolatum heated to about 130°–150° F., preferably about 140° F. (about 60° C.), or liquid soap at room temperature (about 62°–74° F.). When the intermediate tubes 3' are withdrawn from the hot petrolatum, petrolatum will cool and solidify to form a semi-solid coat 39' on the outer surface 14' and a semi-solid filling 34' in the capillary lumen 6' and the capillary lumen access opening 12' which cooperate to plug the capillary lumen access opening 12' as shown in FIG. 32. As stated above, soap at room temperature will provide the same function as the petrolatum. The intermediate tube is then subjected to a further dipping step wherein the intermediate tube shown in FIG. 32 is dipped in one or more dip tanks so as to strip the coating of bond preventing agent 39' from the portion of the intermediate tube 3' below a location on the outer surface 14' proximate the dashed line designated D in FIGS. 32 and 33 so as to strip the tube of bond preventing agent below that location.

After the intermediate tubes 3' are coated in this manner and the capillary lumen access openings 12' are plugged with bond preventing agent 40', the tubes 3' are then dipped in a series of dip tanks (see FIG. 41) provided to coat the intermediate tube 3' with a polymeric bonding composition, preferably silicone rubber, in a step or steps provided to form the overcoat layer 42', and, following a short drying interval, an outer bactericide release layer 61' is created by dipping the intermediate tube 3' into the silicone rubber/nitrofuran compound mixture or dispersion 17 in the last dip tank 57'. The outer release layer 61' is then air dried for about an hour, and then cured. In order to avoid a poor bond between the release layer 61' and the rest of the tube 3', the release layer 61' is coated only over the uncured silicone rubber overcoat layer 42'. In order to avoid any sagging, elongation or stretching of the resilient sleeve 44' or the balloon portion 58' of the balloon catheter 5' shown in FIG. 35. The catheter 4' is cured in a hot liquid bath at 160° F. for about 15 min., and then cured in hot air at 200° F. for an additional hour. This prevents the sleeve from drooping when the contents of the sleeve are raised to high temperatures. In the preferred methods, the intermediate tube 3' is dipped in silicone rubber in two or more successive dipping steps so that the resulting overcoat layer 42' includes underlying and an overlying layers (not shown), which form an integral part of the balloon catheter 5' and are bonded together, and to the outer surface 14' in the portions thereof, 14a', 14b' and 14d', which are located below the dashed line designated D, between the dashed lines designated B and C, and above the dashed line designated A, respectively. The portion 14d' above line A was not coated prior to the final dipping steps designed to provide the overcoat layer 42', and the portion 14a' below line D was stripped of its coating prior to those steps.

In subsequent steps, the proximal end 30' of the balloon catheter 5' is secured to an end piece 46' to form a completed Foley catheter 4' (shown in FIG. 38). The end piece 46' can include a cap 48' for closing a proximal end access opening 49' to the fluid conduit lumen 8' and can be equipped with a luer valve 50' for engagement in and closure of the proximal capillary lumen access upper opening 52' communicating with the capillary lumen 6'. Prior to the attachment of the end piece 46' to the sleeved balloon catheter 5' to form the completed sleeved Foley catheter 4', the sleeved balloon catheter 5' is preferably allowed to air dry to permit solvents in the overcoat layer 42' to evaporate and is subsequently cured at an elevated temperature. Care is taken to keep the curing temperature below the boiling temperatures of the solvent so as to prevent unsightly bubbling of the solvent within the overcoat layer 42'. Because the overcoat layer 42' is preferably made of the same polymeric bonding composition, even though it may be created in a plurality of dipping steps, it is represented in FIGS. 35–39 as a single overcoat layer 42'. It will be appreciated, however, that this single overcoat layer 42' may or may not represent an integral layer formed in a series of dipping steps wherein there may be any number of underlying or overlying layers. The completed Foley catheter 4' also includes a fluid conduit access opening 56' in an exterior surface 62' of the completed Foley catheter 4'. The fluid conduit access opening 56' communicates with the fluid conduit lumen 8'.

Referring now also to FIG. 37, the independence and stretchability of the resilient sleeve 44' is illustrated. The resilient sleeve 44', which includes goth the overcoat layer 42' and the release layer 61', not only has a narrower thickness than the inner wall 21' of the catheter 5', but it is also more flexible, more stretchable, and preferably less rigid than the inner wall 21'. The lubricating substance 38' contained in the sleeve cavity 45' permits the sleeve 44' to slide along and in respect to the outer surface 14' while in lubricated contact therewith and when stretched independently thereof. As illustrated in FIG. 37, the resilient sleeve 44' can be twisted in respect to the inner wall 21' without twisting the inner wall 21' or the respective lumens, 6' and 8'. The resilient sleeve 44' can also be stretched without stretching the inner wall 21' of the catheter 5'. As stated hereinabove, this enables the resilient sleeve 44' to stay in relative contact with or in adherence to adjacent body tissues (not shown) with which the resilient sleeve 44' is in contact with even when the remaining portions of the sleeved balloon catheter 5', such as the inner wall 21', are forced to move in response to forces impacting on the catheter 5' at other points along its length. The resilient sleeve 44 can also change from its initial circumferential shape to a more ribbon-like oval shape in order to match the shape or contour of the passageway in which it resides. The volume of the sleeve cavity 45' will preferably increase the outside diameter of the catheter proximate the sleeve portion at least about 5%, preferably about 10%, more preferably about 20%, even more preferably about 25%, even more preferably about 35%, and even more preferably about 50%. It is conceivable that applications will also be found where the thickness of the lubricating substance in the sleeve cavity 45 is increased so as to increase the volume of the sleeve cavity such that the outside diameter of the catheter proximate the sleeve 44 will be increased from about 50 to 100, or 50 to 200% or more depending on the particular application. The important factor is that the sleeve be soft and compliant so that it can conform to the shape of the particular passageway in which it resides and, at the same time fill the passageway so as to limit the passage of fluids along either the wall of the passageway or the exterior surface of the catheter, and at the same time, to allow the inner conduit portion of the catheter move relatively independently of the exterior surface of the sleeve 44' of the catheter.

In preferred methods in accordance with the present invention, the end piece 46' is made by a process of injection molding. Preferably, the proximal end 30' of the sleeved balloon catheter 5' is inserted into an injection molding apparatus (not shown) after the overcoat layer 42' and the release layer 61' have been cured. However, it will be appreciated that the end piece 46' can be added to the intermediate tube 3' prior to the initiation of the dipping process. A polymeric bonding composition, preferably silicone rubber, is then injected into the mold (not shown) and the end piece 46' is molded onto the proximal end 30' of the balloon catheter 5' to make the completed Foley catheter 4' shown in FIG. 38. Following further drying, curing steps, where deemed necessary given the type of polymeric bonding composition or compositions used to make the completed Foley catheter 4', the completed catheter 4' is tested to see if it is functional and if it has any leaks. This testing can be done before or after the fluid conduit access opening 56' is created in the exterior surface 62' to communicate with the fluid conduit lumen 8'.

In order to test the integrity of the completed catheter 4', prior to engaging the plug 50' in the proximal capillary lumen access opening 52' in the end piece 46', the proximal capillary lumen access opening 52' is slipped over a hot water nozzle (not shown), and a measured amount of a hot aqueous solution, preferably water or water containing a trace of surfactant, at a temperature of between about 120°–160° F., preferably about 140° F., is pumped into the capillary lumen 6' from a standard hot water heater (not shown) by a commercially available water pump (not shown) such that the balloon portion 58' is expanded. It will be appreciated that higher or lower temperatures can be used so long as the desired coating properties for the particular application desired can be obtained. The balloon portion 58' of the overcoat layer 42' is the portion of the overcoat layer 42' which is not bonded to the outer surface 14' of the intermediate tube 3' proximate a balloon cavity 54'. The balloon portion 58' of the overcoat layer 42' cooperates with the portion 14c' of the outer surface 14' which remained coated with the bond preventing agent prior to the step of dipping the intermediate tube 3' in the polymeric bonding composition, to define the balloon cavity 54'. The balloon cavity 54' communicates with the capillary lumen 6' via the Capillary lumen access opening 12'. When the hot water solution is pumped or injected into the capillary access lumen 6' to test the completed catheter 4' and the balloon portion 58', the balloon portion 58' and the balloon cavity 54' are expanded. If there is a significant lack of integrity in the balloon portion 58' it will be exposed when the water is introduced in this manner. In addition to testing the balloon portion 58', the water solution will also remove the remaining bond preventing agent in the balloon lumen 54' and the capillary lumen 6' when it is removed. Although some of the bond preventing agent may come out of the capillary lumen 6' via the proximal capillary lumen access opening 52' during the step of curing the overcoat layer 42', the hot aqueous solution is generally believed to remove most of the bond preventing agent, although a residue may remain.

Following the preliminary test, which relies on a visual observation to determine whether there is any lack of integrity, a further test is used to obtain further assurance that there are no leaks in the balloon portion 58. This further test is accomplished by engaging the proximal capillary lumen accessing opening 52' to the nozzle of a commercially available leak tester (not shown). One such device is a Model No. 6510 Caps Tester from Caps Himmelstein (Hoffman Estates, Ill. 60195). Once the completed catheter 4' is tightly secured over the nozzle, an electrical switch, such as a hand switch or, preferably, a foot pedal, is used to release a measured blast of air into the capillary lumen 6'. When the air is introduced into the capillary lumen 6' it also enters the balloon cavity 54' via the capillary lumen access opening 12' and inflates the balloon portion 58' and, thereby, expands the balloon cavity 54'. The leak tester is designed to sense any loss of pressure once the balloon portion 58' is inflated, and will given an indication, therefore, if there are any measurable leaks. After this test is completed, the completed sleeved Foley catheters 4' that have passed all tests, are then packaged, preferably in a material which breathes such as Tyvek# (from DuPont), and boxed. The boxes are then sterilized with ETO (Ethylene Oxide) and then stored for shipment.

Referring now specifically to FIGS. 43–49, the present invention provides an elongated catheter 4''' (see FIG. 49) having an interior surface 7''' and an exterior surface 9'''. The interior surface 7''' defines a lumen 8'''. The elongated catheter 4''' is preferably made from a tube 2''' (see FIG. 43) which is eventually coated with an overcoat layer 42''' of a resilient polymeric material which binds to an outer surface 14''' of the tube 2''' unless the bonding of the polymeric material is prevented by other materials or means on the outer surface 14'''.

The overcoat layer 42 of the elongated catheter 4''' in accordance with the present invention, includes a sleeve 44''' which encircles a sleeve cavity 45''' which contains lubricating material 38'''. The lubricating material or substance 38''' is effective to permit the sleeve 44''' to slide along the outer surface 14''' of the tube 2''' proximate the sleeve 44''' while in lubricated contact with the outer surface 14'''. When applied in sufficient thicknesses, the lubricating material serves to separate the soft outer sleeve 44''' from the tube 2''', such that the outer sleeve 44''' provides a soft, cushioned, compliant exterior surface which can adapt and conform under slight pressures to the shape of the passageway in which it is inserted or residing. Depending on the catheter application and/or type, the amount of the lubricating substance 38''' and the sleeve cavity 45''' can be minimized to provide for only a limited increase in the outer diameter of the catheter proximate the outer sleeve 44'''. The outer sleeve 44''' is coated with an outer bactericide release layer 61''' similar to that described hereinabove. In other cases, a soft, cushioned, compliant sleeve which can adapt its shape is desirable. In these embodiments, there is a relatively thick coating of lubricant material 38''' in the sleeve cavity 45''' which will give the sleeve 44''' a balloon-like feel and appearance in the exterior surface proximate the sleeve 44'''. The elongated catheter 4''' is preferably made of a flexible elastomeric material such as latex, silicone rubber or the like, most preferably silicone rubber. The lubricating material or substance 38''' is preferably any biocompatible lubricating substance which is effective to permit respective polymeric surfaces to slide with respect to one another when in lubricated contact therewith. Preferably, the lubricating substance 38''' is a hydrophobic oil or other petroleum based product or a water-soluble soap, detergent or the like, either of which is effective to lubricate polymeric surfaces and to generally prevent bonding thereto by other polymeric substances when coated thereby. In a preferred embodiment, the lubricating substance 38''' is petrolatum.

The first step in making an elongated catheter 4''' in accordance with the method of the present invention is to provide a tube 2''' having an outer surface 14''' and an inner surface 7''' defining a first lumen 8'''. The distal end 16''' of the tube 2''' is preferably inserted into a molding apparatus (not shown) designed to mould a tip 20''' on the distal end 16''' of the tube 2''' to form the intermediate tube 3''' (see FIG. 44). In a preferred process of the present invention, the intermediate tube 3''' is then secured on a support rod 26''' of a rack or pellet 2 4''' which preferably includes a plurality of support rods 26'''. Preferably, a plurality of intermediate tubes 3''' are secured on the plurality of support rods prior to subjecting the intermediate tubes 3''' secured on the support rods 26''' to a series of dipping steps in the preferred process.

Figure 47:
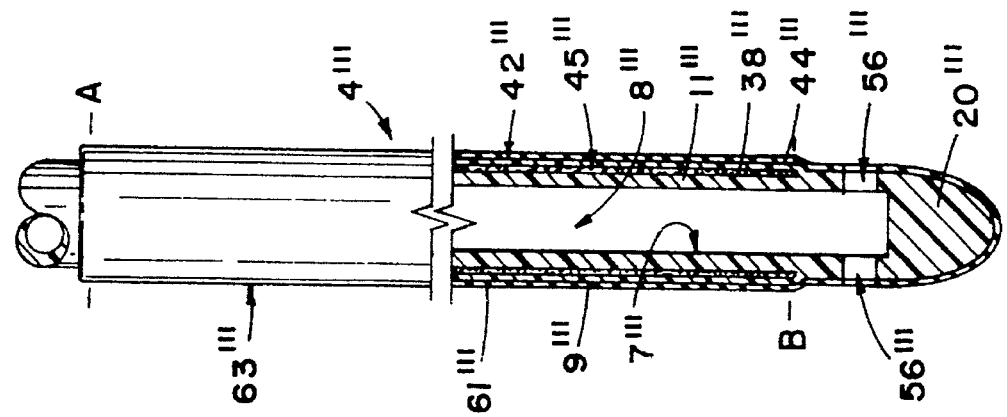
FIG. 47 is a transverse sectional schematic view of the alternate intermediate tube shown in FIG. 46 following a subsequent dipping step or steps in which an overcoat layer is formed over the outer surface thereof.

After the intermediate tube 3''' is formed from the initial tube 2''', the outer surface is coated from the lowest portion of the tip 20''' up to a location on the outer surface 14''' designated by the dashed line A, as shown in FIG. 45, with the lubricating substance. Subsequently, the lubricating substance coating the outer surface 14 of the tube below a location proximate the dashed line designated B, as shown in FIGS. 45 and 46, is stripped from the outer surface 14''' and the tip 20'''. The intermediate tube 3''' is then coated with a resilient polymeric bonding composition which forms the overcoat layer 42'''. The overcoat layer 42''' bonds to the tip 20''' and a portion of the outer surface 14a''' below the dash line designated B, and to a portion of the outer surface 14b''' above the line designated A. In the area proximate to a portion of the outer surface 14c''' between the dash lines designated A and B, respectively, which remains coated with lubricating material 38''', the overcoat layer 42''' forms a sleeve 44''' which encircles the lubricating material 38''' coating the portion of the outer surface 14a''' between the dash lines designated A and B, which cooperates with the sleeve 44''' to define the sleeve cavity 45''' in which the lubricating material 38''' proximate the sleeve 44''' is contained. After the overcoat layer 42''' is formed upon the intermediate tube 3''', an outer bactericide release layer 61''' is formed and a pair of fluid conduit openings 56 are preferably created, most preferably punched, to permit fluid to pass into or out of the lumen 8''' proximate the distal end 16'''. It will be appreciated that, although the overcoat layer 42''' and the wall 11''' of the tube 2''' are shown in FIG. 49 to be separate elements, when made of identical polymeric materials, as is the case with the most preferred embodiments of the present invention which are made of silicone rubber, the wall 11''' and the overcoat layer 42''' will be bonded together where they interface with one another so that it is virtually impossible to distinguish between the two and so that there is preferably no part line in spite of the fact that a part line is shown in FIGS. 47 and 49. In the preferred embodiments, where these elements are enjoined together, it will be appreciated that they form an integral membrane or wall.

The specific procedures used to form the present elongated catheter 4''' will include steps similar to the steps used for similar purposes as described hereinabove.

In the Applicants' use of the preferred methods of the present invention, balloon and sleeve fabrication is almost completely automated. Entire sets of sleeved balloon catheters 5' are manufactured simultaneously. The preferred pallet 24 has 400 spring steel support rods 26 attached to a pallet in 20 rows of 20 rods, wherein each of the rods 26 is about 1 inch from each adjacent rod. Single and double lumen tubing (not shown) is preferably made by extrusion processes known to those of skill in the art. The tubes 2 and 2' are cut to length as the tubing leaves the extruder (not shown). An opening 12' is created in the outer surface 14' of the double lumen tubes 2', preferably with a hollow drill bit or drill tube (not shown), so as to communicate with the capillary lumen 6' in those tubes 2'. The distal portion 6a' of the capillary lumen 6', located between the distal end 16' of the tube 2' and the capillary lumen access opening 12', is then injected with a measured amount of a polymeric bonding composition, preferably silicone rubber, so that the distal portion 6a' is filled and sealed. A rounded tip 20' is then formed at the distal end 16' of the double lumen tube 2', preferably by inserting the tube 2' in a molding device (not shown).

Referring now also to FIG. 39, another preferred embodiment of the present invention is illustrated in this embodiment of the present invention as sleeved Foley catheter 4". It is very similar to the catheter shown in FIG. 38 except that the space between the balloon cavity 54" and the sleeve cavity 45" has been decreased so that it will accommodate the urethral sphincter of the bladder. In addition, the volume of the lubricating substance 38"" in the sleeve cavity 45" is significantly more than that shown in FIG. 38. This is accomplished by increasing the thickness of the lubricating substance 38 which is coated onto the intermediate tube 3' carrying the manufacturing process. The increase in the thickness of the lubricating substance 38" allows the sleeved Foley catheter 4" to provide a very soft, "cushy", conforming exterior surface 9" proximate the sleeve 44" which can accommodate variations in the surfaces with which the catheter 4" comes into contact.

Referring now also to FIG. 40, the sleeved Foley catheter 4" shown in FIG. 39 is shown when inserted into a urethral tract 74 of a woman 70 the balloon portion 58" of the catheter 4" resides within the bladder 72 of the woman 70. The balloon portion 58" is expanded to retain the catheter 4" in the urethral tract 74. The harsh volume of lubricating substance 38" in the sleeve cavity 45" is shown to provide a exterior surface 9" proximate the sleeve 44" which conforms to the wall of the urethral tract 74. The lubricating substance 38" also allows the inner wall 46" or conduit portion 46" of the catheter 4" to move back and forth within the urethral tract 74" to a limited degree without disrupting the interface between the exterior surface 9" proximate the sleeve 44" and the adjacent body tissues of the urethral tract. This allows the catheter 4" to move in all directions to a limited degree without disrupting this interface, thereby increasing the comfort of the patient in which the catheter 4" resides.

In the most preferred embodiments of the present method, 400 of the intermediate tubes 3' are then mounted vertically on rigid spring steel support rods 26' on a pallet 24' in the manner previously described. The pallet 24' is then moved via a transporting mechanism 22 (see FIG. 28) over a series of dip tanks as follows in the following example which will further disclose preferred elements of the present invention.

EXAMPLE I.

(A) The pallet 24' is stopped over a first tank 33', which contains white USP petrolatum heated to about 60° C. (about 140° F.). The tank is raised so as to immerse the intermediate tubes 3' into the petrolatum to such a depth that the petrolatum reaches the proximal end of the desired sleeve location. The dip tank 33' is then lowered and a portion of the outer surface 14' of the intermediate tubes 3' are coated with petrolatum. This portion extends from the general point at which the proximal end of the resilient sleeve 44' will begin, to the distal end 20a' of the tip 20' of the intermediate tube 3'. This step is repeated when it is desireable to build up the thickness of the lubricating substance and the resulting volume of the sleeve cavity so as to increase the resulting increase in the outside diameter of the particular catheter over the circumferential diameter of the conduit portion or tube 2 or 2' of this present invention.

(B) The pallet 24' is then automatically advanced and stopped over a second dip tank 35' which contains white USP petrolatum heated to about 120° C. (about 250° F.). The second dip tank 35' is raised so as to immerse the intermediate tubes 3' into the super-heated petrolatum so that the super-heated petrolatum comes into contact with the petrolatum coating 38' on outer surface 14' of the intermediate tube 3' from the prior dipping step up to a general location where a distal end of the resilient sleeve 44' will end. The second dip tank 35' is then lowered. This dipping step causes the coating of petrolatum from the prior dipping step to be largely removed from the portions 14a' the outer surface 14' below a location where the distal end of the resilient sleeve 44' will be generally located (designated by dashed line B) to the distal end 20a' of the tip 20' of the intermediate tube 3'. Some residual petrolatum may remain on the outer surface 14' of the intermediate tube 3' in this area of the outer surface 14'. However, most of the petrolatum is removed.

(C) The pallet 24' is then automatically advanced and stopped over a third dip tank 37' containing mineral spirits heated to about 200° F. The third dip tank 37' is then raised so as to immerse the intermediate tubes 3' into the mineral spirits to the same depth as they were immersed in the super-heated petrolatum in the second dip tank 35'. The tank 37' is then lowered and all but a trace amount of the petrolatum is removed from the outer surface 14' located generally below the dashed line B, which will eventually be proximate the sleeve 44'.

(D) The pallet 24' is then automatically advanced and stopped over a fourth dip tank 40' containing a volatile organic solvent such as toluene, trichloromethane or the like. The fourth tank 40' is then raised to immerse the intermediate catheters 3 to the same depth as previously immersed in the second and third tanks 35' and 37+, thereby removing essentially all traces of the petrolatum from this portion of the outer surface 14'. The intermediate catheter tube 3' now has a band 38' of semi-solid petrolatum located around the axial circumference of the intermediate tube 3' in the location where the sleeve cavity 45' will be created.

Figure 19:
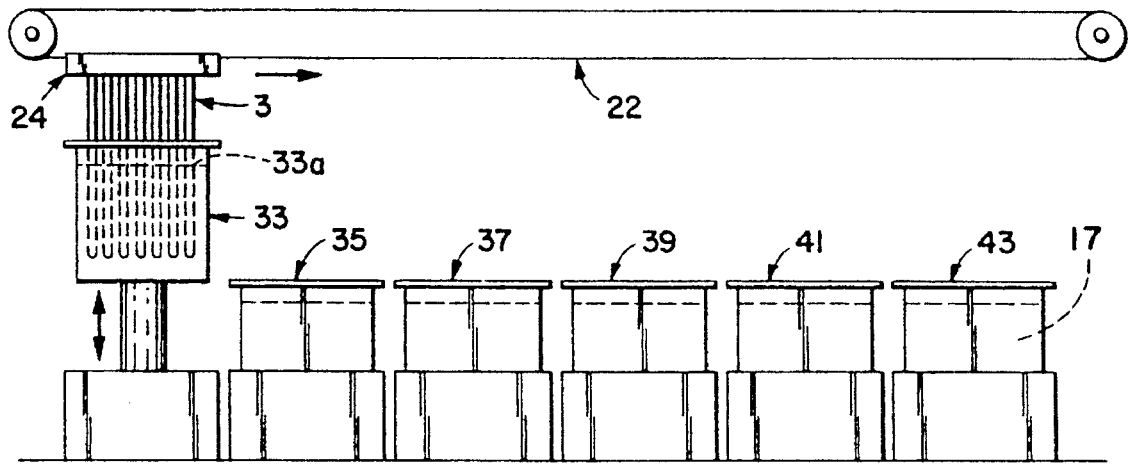
FIG. 19 is a schematic illustration of apparatus used to automate the production of balloon catheters in accordance with the present invention.

(E) The pallet 24' is then stopped over a fifth, sixth, seventh and eighth dip tank, 41', 43', 51' and 53', respectively, where the steps enumerated in steps A, B, C, and D, respectively, are repeated with the following variation. When the pallet 24' is stopped over the fifth dip tank 41', the intermediate tubes 3' are immersed only up to a location proximate the dashed line designated C as shown in FIGS. 18 and 19. When the pallet 24' is subsequently stopped in series over dip tanks 43', 47' and 49', the intermediate tubes 3' on the pallet 24' are only immersed up to a location proximate the dashed line D as shown in FIGS. 32 and 33. Following these steps, the petrolatum is stripped from the portion 14a' of the outer surface 14' located below the location proximate the dashed line designated line D. The petrolatum not only coats the portion 14c' of the outer surface 14' located in this area, but also fills a portion of the capillary lumen 6' and plugs the capillary lumen access opening 12', which will eventually be used to inflate the balloon portion 58' of the completed Foley catheter 4'.

(F) After the last of these dip tanks (53') is lowered, the pallet 24' is automatically advanced to a ninth dip tank 55' containing a low-solids silicone rubber/solvent dispersion which is effective to minimize any disruption of the integrity of the petrolatum coatings 38' or 40' remaining on the intermediate tube 3' proximate the portions 14e' and 14c' of the outer surface 14' where the sleeve cavity 45' balloon cavity 54' will be created during subsequent dipping steps. The ninth tank 51' is then raised to immerse the intermediate tube 3' in the solution up to a location above the dashed line designated in A in FIG. 33. This step can be subsequently repeated at intervals, preferably allowing time for significant solvent evaporation, either in the same tank or in a subsequent tank containing a greater concentration of silicone rubber, until the overcoat layer 42' and the balloon portion 58' of the overcoat layer 42' have a desired balloon thickness. The dip tank 55' is then lowered, and the overcoat layer 42' is allowed to air dry for about 15 minutes. The pallet 24' is advanced to a tenth dip tank 57 containing a silicone rubber/nitrofuran compound fluid mixture or dispersion 17', and the tubes 3' are completely immersed again. The preferred thickness of the resilient sleeve 44' and the balloon portion 58' is 17.5 thousandths of an inch (plus or minus 2.5 thousandths of an inch), although a modest increase is not considered to be detrimental to the function thereof. Where subsequent silicone rubber dip tanks are provided, the concentration of silicone rubber in the subsequent tanks are preferably greater than the concentration of the silicone rubber in the ninth tank 51. It is also desirable to alter the silicone rubber used in a final coating to provide greater sheen and a smoother finish, however, the concentration and the solvent may be adjusted as deemed appropriate.

(G) The pallet 24' is then advanced through a drying area where solvents are allowed to evaporate, and then through a two port (liquid/hot air) heat cure step, where the sleeved balloon catheters 5' formed by this process are cured, first in a hot liquid bath at 160° F. for 15 minutes, and then in hot air (200° F.), or at a temperature just below the boiling point of any solvent used in any of the silicone rubber dip dispersions, for an hour. For toluene this temperature is about 200° F.

(H) After the heat cure, the sleeved balloon catheters 5' are allowed to cool and are then removed from the support rods 26'. The proximal ends 30' of each of the balloon catheters 4 is then inserted into an injection molding apparatus (not shown), which forms the end piece 46' of the completed sleeved Foley catheter 4'.

(I) The completed Foley catheters 5 are then finished by punching a fluid conduit access opening 56' in the exterior surface 61' such that it communicates with the fluid conduit lumen 8' in a location below or distal to the balloon portion 58' of the overcoat layer 42'.

Figure 42A:
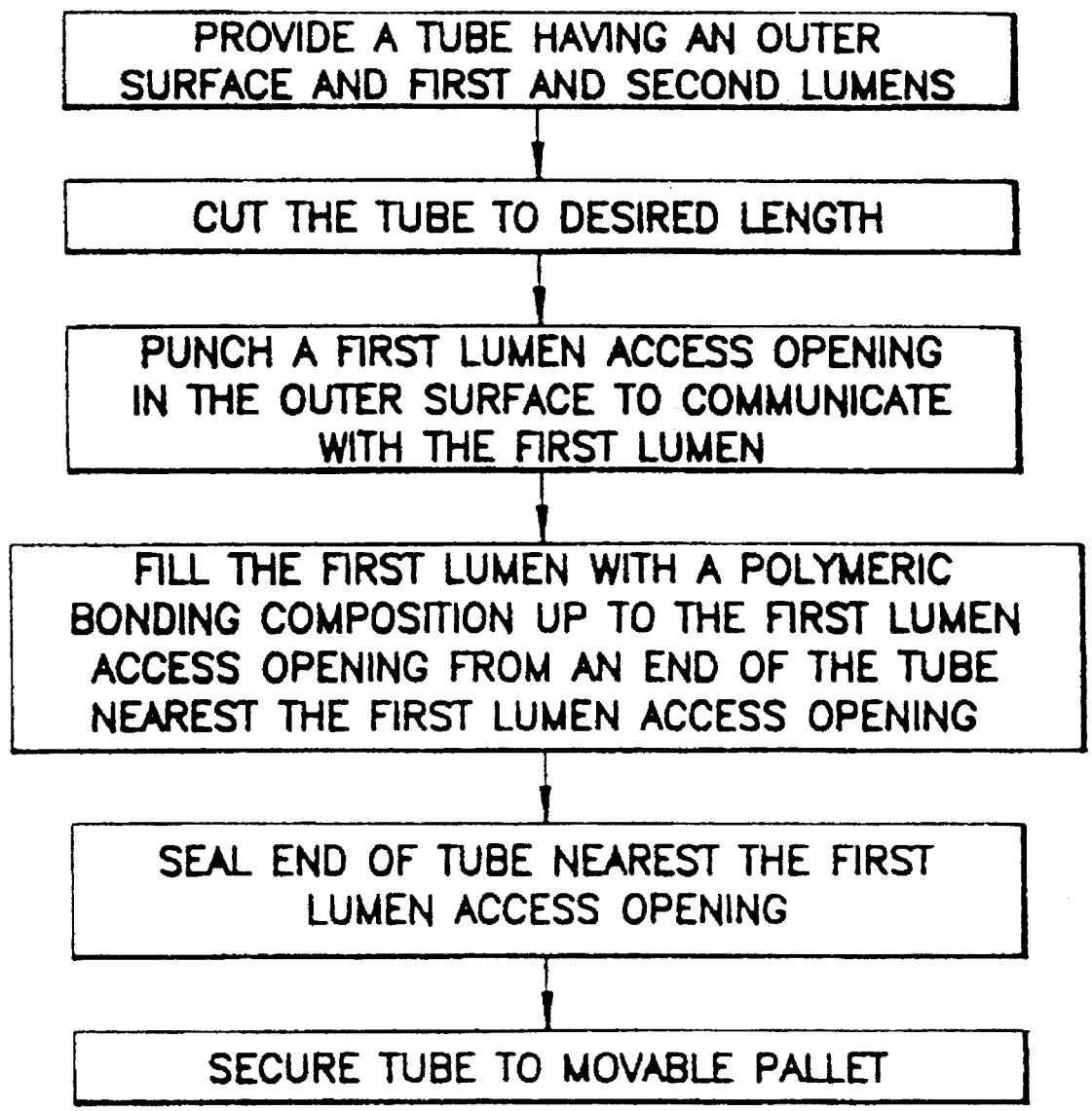
FIG. 42a, 42b and 42c are flow charts illustrating certain steps in methods in accordance with the present invention.
Figure 42B:
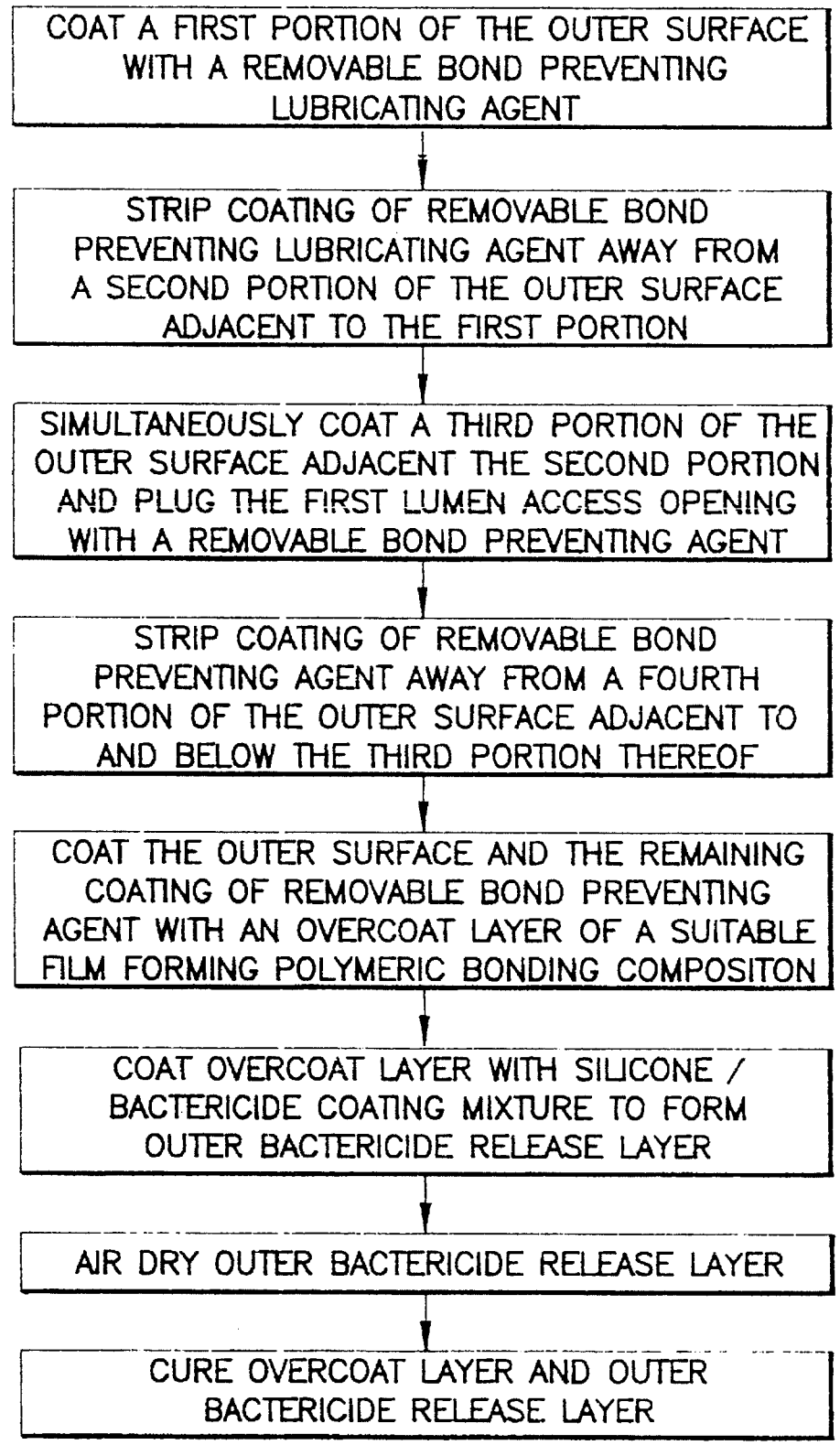
Figure 42C:
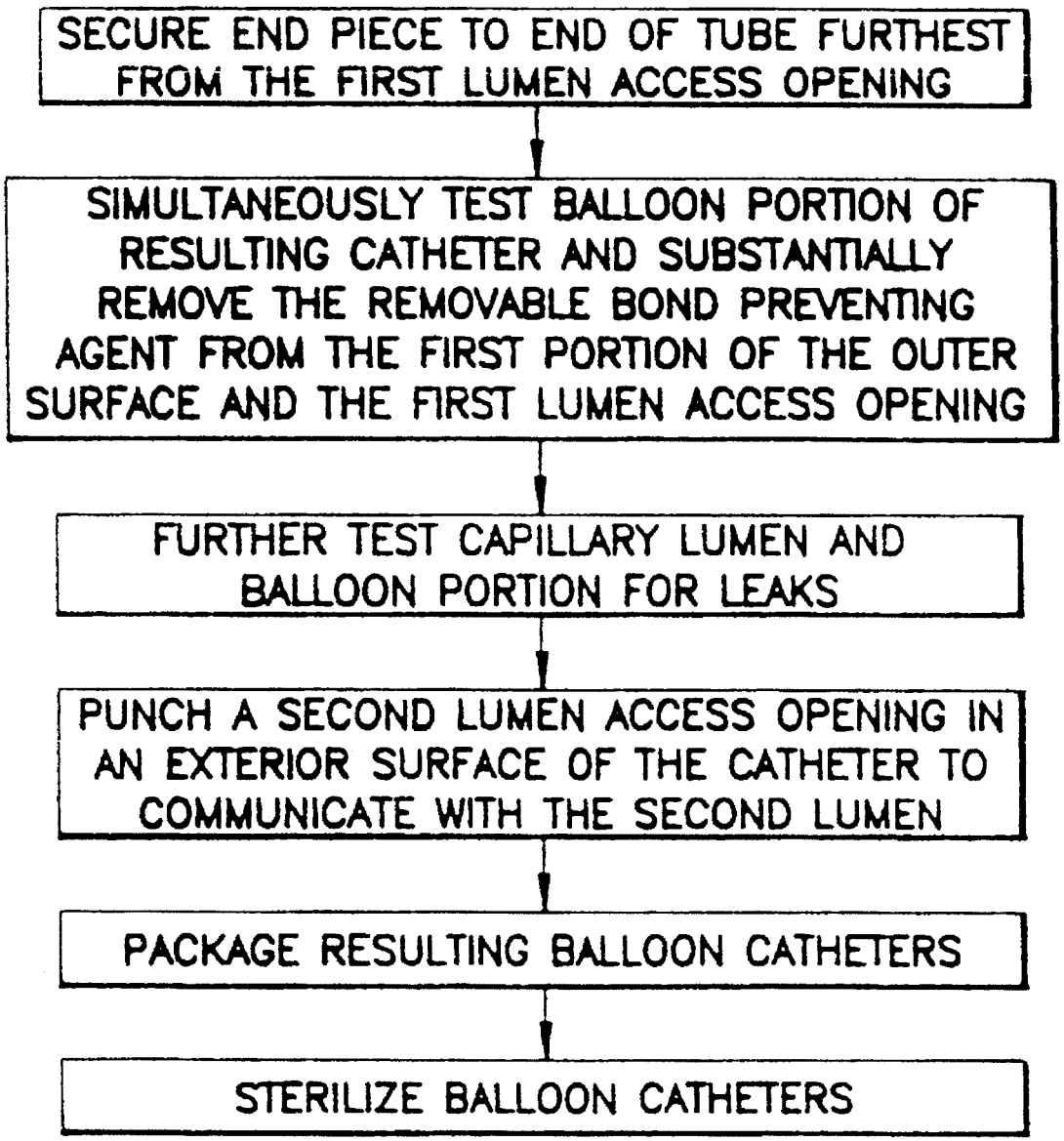

(J) The completed Foley catheters 4' are then sent through the test sequence described hereinabove, during which the balloon portion 58' of each completed Foley catheter 4' is inflated and the petrolatum band 40' within the balloon cavity 54' is largely removed. Referring now also to FIGS. 42a, 42b and 42c, the present invention provides a method of making sleeved Foley catheters 4' including the following steps:

(A) Providing a tube having an outer surface and first and second lumens;

(B) Cutting the tube to a desired length;

(C) Creating a first lumen access opening in the outer surface to communicate with the first lumen;

(D) Filling the first lumen with a polymeric bonding composition up to the first lumen access opening from an end nearest the first lumen access opening;

(E) Sealing the end of the tube nearest the first lumen access opening; and (F) Securing the tube to a movable pallet.

These steps are followed by the following steps:

(A) Coating a first portion of the outer surface and plugging the first lumen access opening with a removable bond preventing lubricating agent;

(B) Stripping the coating of removable bond preventing lubricating agent away from a second portion of the outer surface adjacent to the first portion;

(C) Simultaneously coating a third portion of the outer surface adjacent to the second portion thereof and plugging the first lumen access opening with a removable bond preventing agent;

(D) Stripping the coating of removable bond preventing agent away from a fourth portion of the outer surface adjacent to and below the third portion thereof;

(E) Coating the outer surface and the remaining coating of removable bond preventing agent with an overcoat layer of a suitable film forming polymeric bonding composition;

(F) Coating the overcoat layer with a silicone rubber/ bactericide coating mixture to form an outer bactericide release layer;

(G) Air drying outer bactericide release layer; and (H) Curing the overcoat layer.

Following those steps, methods of the present invention include the following steps:

(A) Securing an end piece to the end of the tube furthest from the first lumen access opening;

(B) Simultaneously testing the balloon portion of the resulting catheter and substantially removing the removable preventing bond agent from the first portion of the outer surface and the first lumen access opening;

(C) Further testing the catheter capillary lumen and the balloon portion for leaks;

(D) Punching a second lumen access opening in an exterior surface of the catheter to communicate with the second lumen;

(E) Packaging the resulting sleeved Foley catheters; and (F) Sterilizing the sleeved Foley catheters.

In another preferred embodiment of the present invention, following the securing of a plurality of intermediate tubes 3' to the transportable pallet 24', balloon catheters are produced as follows:

(A) The pallet 24' is stopped over a first tank 33', which contains white USP petrolatum heated to about 60° C. That tank 33' is then raised so as to immerse the intermediate tubes 3' into the petrolatum to such a depth that the petrolatum reaches the proximal end of the desired resilient sleeve location proximate the dashed line designated A in FIG. 29. The dip tank 33' is then lowered and a portion of the outer surface 14' of the intermediate tubes 3' are coated with petrolatum. This portion extends from the general point at which the proximal end of the resilient sleeve 44' will begin, to the distal end 2a' of the tip 20' of each intermediate tube 3'. In other embodiments, this step can be repeated to increase the thickness of the lubricant coating 38', as well as the ultimate volume of the sleeve cavity 45' and the size of the outside diameter of the catheter 5' proximate the sleeve 44'.

(B) The steps outlined in paragraphs B, C and D of Example I presented hereinabove, are then followed generally as outlined in Example I.

(C) The pallet 24' is then stopped over a fifth dip tank 41', which contains a liquid soap (Liquid Ivory Soap from Proctor & Gamble Co., Cincinnati, Ohio 45202). The soap is held at room temperature (between about 6°–80° F., preferably 65°–72° F.). The fifth dip tank 41' is raised so as to immerse the intermediate tubes 3' into the liquid soap so that the soap coats the tubes 3' up to the dashed line designated by the letter C in FIG. 32. The dip tank 41' is then lowered and the liquid soap forms a semi-solid coating 40' on the outer surface 14' of each of the intermediate tubes 3' extending from line designated C to the distal end 20a' of the tip 20' of each of the intermediate tubes 3'.

(D) The pallet 24 is then automatically advanced and stopped over a sixth dip tank 43' which contains an aqueous solution containing a trace of a suitable wetting agent or surfactant. In a preferred embodiment, three gallons of water is mixed with two ounces of a suitable surfactant. The surfactant will generally be less than one percent of the total volume of the solution. A sixth dip tank 43' is then raised so as to immerse the intermediate tubes 3' in the aqueous fluid up to the dashed line designated by the letter D in FIGS. 32 and 33. The sixth dip tank 43' is then lowered and the semi-solid liquid soap coating the portion 14a' of the outer surface 14' below the dashed line designated D is substantially removed.

(E) The pallet 24' is then automatically advanced and stopped over a seventh dip tank 51' containing water. The seventh dip tank 51' is then raised and the intermediate tubes 3' are immersed in the water up to the line designated D as in the prior dipping step. The seventh dip tank 51' is then lowered and virtually all of the liquid soap is removed from the portion 14a' of the outer surface 14' below the line designated D.

(F) The pallet 24' is then automatically advanced and stopped over a eighth dip tank 53' containing a low-solids silicone rubber/solvent dispersion which is effective to minimize any disruption of the integrity of the liquid soap coating 40' remaining on each of the intermediate tubes proximate the portion 14c' of the outer surface 14' where the balloon cavity 54 will be created during subsequent dipping steps (the portion between the dashed lines designated C and D). The eighth tank 53' is then raised to immerse intermediate tubes 3' in the silicone rubber dispersion. It will be appreciated that any suitable solvent for providing a suitable dispersion of silicone rubber and coating the particular lubricating agent may be used. It is also believed to be possible to use aqueous solvents, however, they are not preferred at present. It will also be appreciated that this step can be repeated at subsequent intervals, preferably long enough to permit significant solvent evaporation, to add to the thickness of the overcoat layer 42' and the balloon portion 58' of the overcoat layer 42'. However, further steps, involving different solutions can also follow.

(G) The fourth dip tank 39' is then lowered and the silicone rubber, coating portions of the outer surface 14' as well as the coating of petrolatum 38' and the coating of soap 40', is allowed to dry. The pallet 24' is then advanced again to a ninth dip tank 55' containing a different silicone rubber dispersions having a solids content which is higher than the solids content in the eighth dip tank 53'. The intermediate tubes 31' are immersed again in the subsequent silicone rubber dispersion when the ninth dip tank 55' is raised. The ninth dip tank 55' is then lowered, and the silicone rubber, coating the tubes 3', is allowed to dry.

(H) The pallet 24' is then automatically advanced again to a tenth dip tank 53 containing a silicone rubber/nitrofuran compound fluid mixture 17' including a silicone rubber and silicone fluid in trichloroethane, mixed with a nitrofuran compound, preferably nitrofurazone particles having a mean particle diameter of 100 microns or less. The tubes 3' are dipped again as before and the tenth dip tank 51' is then lowered and the silicone rubber coating the tubes 3' is allowed to dry.

(G) The pallet 24' is then advanced through a drying step followed by a two-part (liquid/hot air) heat cure step, and each completed sleeved balloon catheter 5' is then secured to an end piece 46', tested, provided with a fluid conduit access opening 56', packaged and sterilized.

The automated system that Applicants claim will permit completed sleeved Foley catheters 4' to be manufactured at the rate of about 1,600 catheters per hour. Because virtually no handwork is involved in the balloon and sleeve construction, the catheters 4' produced will be consistent and of very high quality. The exterior surface 62' is smoother than hand-glued balloons, and the outside diameter of the balloon portion 58' is essentially identical to the outside diameter of other portions of the completed Foley catheters 4'. It will be appreciated that larger outside diameter balloon portions are undesirable since they are somewhat more difficult to insert and withdraw, and cause additional trauma upon withdrawal. In addition, by eliminating the hand labor involved in adhering the balloon portion 58' to the intermediate tube 3' in the manufacture of silicone rubber balloon catheters 5', by specifically eliminating the separate step of fabricating the balloon portion, which also requires hand labor, and by eliminating the significant impact on yield resulting from hand processing errors, the applicants' new process will permit direct production cost for silicone rubber balloon catheters of all types to be reduced by about 25–50% over the cost estimated for the prior art silicone rubber balloon catheters.

It is to be understood, however, that even though numerous characteristics and advantages of the present invention have been set forth in the foregoing description, together with details of the structure and function of the invention, the sequence or order of the specific steps, or the actual compositions, solvents, temperatures, environmental conditions and the like employed for each step, it will be appreciated the disclosure is illustrative only, and that changes may be made in detail, especially in matters of shape, size, arrangement of parts or sequence or elements of events within the principles of the invention to the full extent indicated by the broad general meaning of the terms in which the appended claims are expressed.

What is claimed is:

1. A method for making a sustained release bactericidal catheter, the catheter being made from a tube, the tube having an inner surface, defining an inner lumen passing through the tube, and an uncured silicone rubber outer surface, said method comprising the steps of:

(a) providing an antibacterial agent containing mixture including uncured silicone rubber, a silicone fluid, and an effective amount of a solid particulate antibacterial agent, wherein the antibacterial agent is a nitrofuran compound having a solubility in water of 0.2% by weight or less;

(b) coating at least a portion of the outer surface of the tube with the antibacterial agent containing mixture to form an uncured nitrofuran containing silicone rubber outer layer; and (c) curing the silicone rubber of both the uncured silicone rubber outer surface and the uncured nitrofuran containing silicone rubber outer layer to form a cured antibacterial agent containing silicone rubber outer layer bonded to the silicone rubber outer surface, wherein the step of providing an antibacterial agent containing mixture includes providing an antibacterial agent containing mixture containing a sufficient amount the nitrofuran compound that the cured antibacterial agent containing silicone rubber outer layer contains about 10 to about 60 percent by weight of the nitrofuran compound.

2. A method for making a urinary catheter, the catheter being made from a tube, the tube having an inner surface, defining an inner lumen passing through the tube, and an uncured silicone rubber outer surface, said method comprising the steps of:

(a) providing an antibacterial agent containing mixture including uncured silicone rubber, a silicone fluid, and an effective amount of a solid particulate antibacterial agent, wherein the antibacterial agent is a nitrofuran compound having a solubility in water of 0.2% by weight or less;

(b) coating at least a portion of the outer surface of the tube with the antibacterial agent containing mixture to form an uncured nitrofuran containing silicone rubber outer layer; and (c) curing the silicone rubber of both the uncured silicone rubber outer surface and the uncured nitrofuran containing silicone rubber outer layer to form a cured antibacterial agent containing silicone rubber outer layer bonded to the silicone rubber outer surface, wherein the step of providing an antibacterial agent containing mixture includes providing an antibacterial agent containing mixture containing a sufficient amount of the nitrofuran compound that the cured antibacterial agent containing silicone rubber outer layer contains about 10 to about 60 percent by weight of the nitrofuran compound.

3. A sustained release bactericidal catheter, the catheter being made by the method comprising the steps of:

(a) providing a tube, the tube having an inner surface, defining an inner lumen passing through the tube, and an uncured silicone rubber outer surface;

(b) providing an antibacterial agent containing mixture including uncured silicone rubber, a silicone fluid, and an effective amount of a solid particulate antibacterial agent, wherein the antibacterial agent is a nitrofuran compound having a solubility in water of 0.2% by weight or less;

(c) coating at least a portion of the outer surface of the tube with the antibacterial agent containing mixture to form an uncured nitrofuran containing silicone rubber outer layer; and (d) curing the silicone rubber of both the uncured silicone rubber outer surface and the uncured nitrofuran containing silicone rubber outer layer to form a cured antibacterial agent containing silicone rubber outer layer bonded to the silicone rubber outer surface, wherein the step of providing an antibacterial agent containing mixture includes providing an antibacterial agent containing mixture containing a sufficient amount the nitrofuran compound that the cured antibacterial agent containing silicone rubber outer layer contains about 10 to about 60 percent by weight of the nitrofuran compound.

4. A urinary catheter, the catheter being made by the method comprising the steps of:

(a) providing a tube, the tube having an inner surface, defining an inner lumen passing through the tube, and an uncured silicone rubber outer surface;

(b) providing an antibacterial agent containing mixture including uncured silicone rubber, a silicone fluid, and an effective amount of a particulate solid antibacterial agent, wherein the antibacterial agent is a nitrofuran compound having a solubility in water of 0.2% by weight or less;

(c) coating at least a portion of the outer surface of the tube with the antibacterial agent containing mixture to form an uncured nitrofuran containing silicone rubber outer layer; and (d) curing the silicone rubber of both the uncured silicone rubber outer surface and the uncured nitrofuran containing silicone rubber outer layer to form a cured antibacterial agent containing silicone rubber outer layer bonded to the silicone rubber outer surface, wherein the step of providing an antibacterial agent containing mixture includes providing an antibacterial agent containing mixture containing a sufficient amount of the nitrofuran compound that the cured antibacterial agent containing silicone rubber outer layer contains about 10 to about 60 percent by weight of the nitrofuran compound.

5. The method of claim 1, wherein the particulate antibacterial agent includes particles having a mean diameter of less than about 500 microns.

6. The method of claim 2, wherein the particulate antibacterial agent includes particles having a mean diameter of less than about 500 microns.

7. The sustained release bactericidal cannula of claim 3, wherein the particulate antibacterial agent includes particles having a mean diameter of less than about 500 microns.

8. The urinary catheter of claim 4, wherein the particulate antibacterial agent includes particles having a mean diameter of less than about 500 microns.

* * * * *

UNITED STATES PATENT AND TRADEMARK OFFICE
CERTIFICATE OF CORRECTION

PATENT NO. : 5,599,321

DATED : FEBRUARY 4, 1997

INVENTOR(S) : CONWAY ET AL.

It is certified that error appears in the above-identified patent and that said Letters Patent is hereby corrected as shown below:

Col. 1, line 33: "TO" should read —to—

Col. 1, line 43: "one' bladder" should read —one's bladder—

Col. 12, line 39: "nitrfurazone" should read —nitrofurazone—

Col. 18, line 54: "Referring" starts a new paragraph

Col. 23, line 24: "Capillary" should read —capillary—

Col. 23, line 60: "Tyvek#" should read –Tyvek$^{TM}$ —

Col 27, line 15: "37+" should read —37'—

Col 29, line 47: "6°–80°F.," should read —60°–80°F.,—

Signed and Sealed this

Fourteenth Day of September, 1999

Q. TODD DICKINSON

Attest:

*Attesting Officer*        *Acting Commissioner of Patents and Trademarks*